(12) United States Patent
Gollasch et al.

(10) Patent No.: US 8,457,743 B2
(45) Date of Patent: Jun. 4, 2013

(54) METHOD OF VAGAL STIMULATION TO TREAT PATIENTS SUFFERING FROM CONGESTIVE HEART FAILURE

(75) Inventors: Maik Gollasch, Berlin (DE); Eckhard Alt, Houston, TX (US)

(73) Assignee: Medtronic, Inc., Minneapolis, MN (US)

( * ) Notice: Subject to any disclaimer, the term of this patent is extended or adjusted under 35 U.S.C. 154(b) by 64 days.

(21) Appl. No.: 12/807,706

(22) Filed: Sep. 11, 2010

(65) Prior Publication Data

US 2011/0087304 A1    Apr. 14, 2011

Related U.S. Application Data

(63) Continuation-in-part of application No. 12/857,140, filed on Aug. 16, 2010, now Pat. No. 8,219,198, which is a continuation of application No. 11/104,389, filed on Apr. 11, 2005, now Pat. No. 7,778,709, which is a continuation-in-part of application No. 10/622,184, filed on Jul. 16, 2003, which is a continuation-in-part of application No. 10/155,771, filed on May 25, 2002, now Pat. No. 6,829,503.

(51) Int. Cl.
*A61N 1/378* (2006.01)

(52) U.S. Cl.
USPC .................................. 607/35; 607/9

(58) Field of Classification Search
USPC .............................. 607/5, 9, 17, 35
See application file for complete search history.

(56) References Cited

U.S. PATENT DOCUMENTS 3,693,625 A    9/1972   Auphan
3,842,843 A   10/1974   Mourot et al.
(Continued)

FOREIGN PATENT DOCUMENTS

WO    WO 2004/032788 A2    4/2004
WO    WO 2007/109272 A2    9/2007

OTHER PUBLICATIONS

Fricke et al., *The Electric Conductivity of and Capacity of Dispersed Systems*; Physics 1931; 1:106-115.

(Continued)

*Primary Examiner* — Brian T Gedeon
(74) *Attorney, Agent, or Firm* — IPLM Group, P.A.

(57) ABSTRACT

An improved method is presented for evaluating the physiological status of a patient diagnosed with congestive heart failure and treating the patient accordingly to alleviate the congestive heart failure. As part of the method, the thoracic or cardiac impedance and ventilation of the particular patient are derived solely from an input consisting of cardiac signals (EKG) generated by electrical energy of the patient's heart as the heart is undergoing its cardiac cycle with a dynamic impedance obtained by subjecting the EKG to alternately high and low input impedances. The derived thoracic impedance and ventilation are used to control the pattern and rate at which stimulating electrical pulses are applied to the patient's vagus nerve by an implanted stimulator, in a manner to deliver therapy to the patient's heart by adjusting the heart rate to a prescribed target rate for alleviating the congestive heart failure. A change in state of the patient from one of rest to one of physical exercise and vice versa detected from the derived impedance and ventilation is accommodated by modifying the vagal stimulation therapy to adjust the patient's heart rate to a new target rate accordingly, while continuing to deliver the therapy for alleviating the congestive heart failure. A closed loop system is preferably employed for the control and adjustment functions.

22 Claims, 13 Drawing Sheets

U.S. PATENT DOCUMENTS

| | | |
|---|---|---|
| 3,906,960 A | 9/1975 | Lehr |
| 4,690,143 A | 9/1987 | Schroeppel |
| 4,884,576 A | 12/1989 | Alt |
| 4,899,758 A | 2/1990 | Finkelstein et al. |
| 4,919,136 A | 4/1990 | Alt |
| 5,003,976 A | 4/1991 | Alt |
| 5,024,222 A | 6/1991 | Thacker |
| 5,331,966 A | 7/1994 | Bennett et al. |
| 5,342,408 A | 8/1994 | deCoriolis et al. |
| 5,643,328 A | 7/1997 | Cooke et al. |
| 5,782,884 A | 7/1998 | Stotts et al. |
| 5,792,197 A | 8/1998 | Nappholz |
| 5,792,205 A | 8/1998 | Alt et al. |
| 5,876,353 A | 3/1999 | Riff |
| 5,899,928 A | 5/1999 | Sholder et al. |
| 5,920,310 A | 7/1999 | Faggin et al. |
| 5,957,861 A | 9/1999 | Combs et al. |
| 5,987,352 A | 11/1999 | Klein et al. |
| 6,080,187 A | 6/2000 | Alt et al. |
| 6,104,949 A | 8/2000 | Pitts Crick |
| 6,190,324 B1 | 2/2001 | Kieval et al. |
| 6,336,903 B1 | 1/2002 | Bardy |
| 6,351,667 B1 | 2/2002 | Godie |
| 6,416,471 B1 | 7/2002 | Kumar et al. |
| 6,445,956 B1 | 9/2002 | Laird et al. |
| 6,456,256 B1 | 9/2002 | Amundson et al. |
| 6,470,212 B1 | 10/2002 | Weijand et al. |
| 6,473,640 B1 | 10/2002 | Erlebacher |
| 6,497,655 B1 | 12/2002 | Linberg et al. |
| 6,512,949 B1 | 1/2003 | Combs et al. |
| 6,512,953 B2 | 1/2003 | Florio et al. |
| 6,600,949 B1 | 7/2003 | Turcott |
| 6,622,041 B2 * | 9/2003 | Terry et al. .......................... 607/9 |
| 6,640,137 B2 | 10/2003 | MacDonald |
| 6,721,597 B1 | 4/2004 | Bardy et al. |
| 6,829,503 B2 | 12/2004 | Alt |
| 8,005,543 B2 * | 8/2011 | Libbus et al. .................... 607/9 |
| 2002/0013613 A1 | 1/2002 | Haller et al. |
| 2002/0055761 A1 | 5/2002 | Mann et al. |
| 2002/0115939 A1 | 8/2002 | Mulligan et al. |
| 2003/0074029 A1 | 4/2003 | Deno et al. |
| 2003/0114898 A1 | 6/2003 | Von Arx et al. |
| 2003/0139783 A1 | 7/2003 | Kilgore et al. |
| 2007/0078492 A1 | 4/2007 | Tozzi et al. |

OTHER PUBLICATIONS

Geddes L. et al., *The Specific Resistance of Biological Material: A Compendium of Data for the Biomedical Engineer and Physiologist*, Medical and Biological Engineering 1967, 5:271-293.

Geddes et al., Medical and Biological Engineering 1967, 11:336-339.

Carter et al., Chest 2004, 125:1431-1 440.

E. Alt et al. For capture detection in connection with cardiac pacing (Pace 1992, 15: 1873-1 879).

Studies published at the 2005 meeting of the American College of Cardiology in Orlando, Florida, USA (CARE-HF study).

Louis, et al., "A systematic review of telemonitoring for the management of heart failure," The European Journal of Heart Failure 5 (2003) 583-590.

Valina et al., "Subcutaneous Impedance Monitoring for Detection of Low Cardiac Output and Fluid Overload," American Heart Association Scientific Sessions 2003, abstract tracking No. 03-SS-A-17350-AHA.

Langreth, "The Doctor Is In: predicting and treating disease will get a whole lot easier when monitors are implanted," Forbes Magazine article dated Sep. 15, 2003.

47 C.F.R. § 95.628.

* cited by examiner

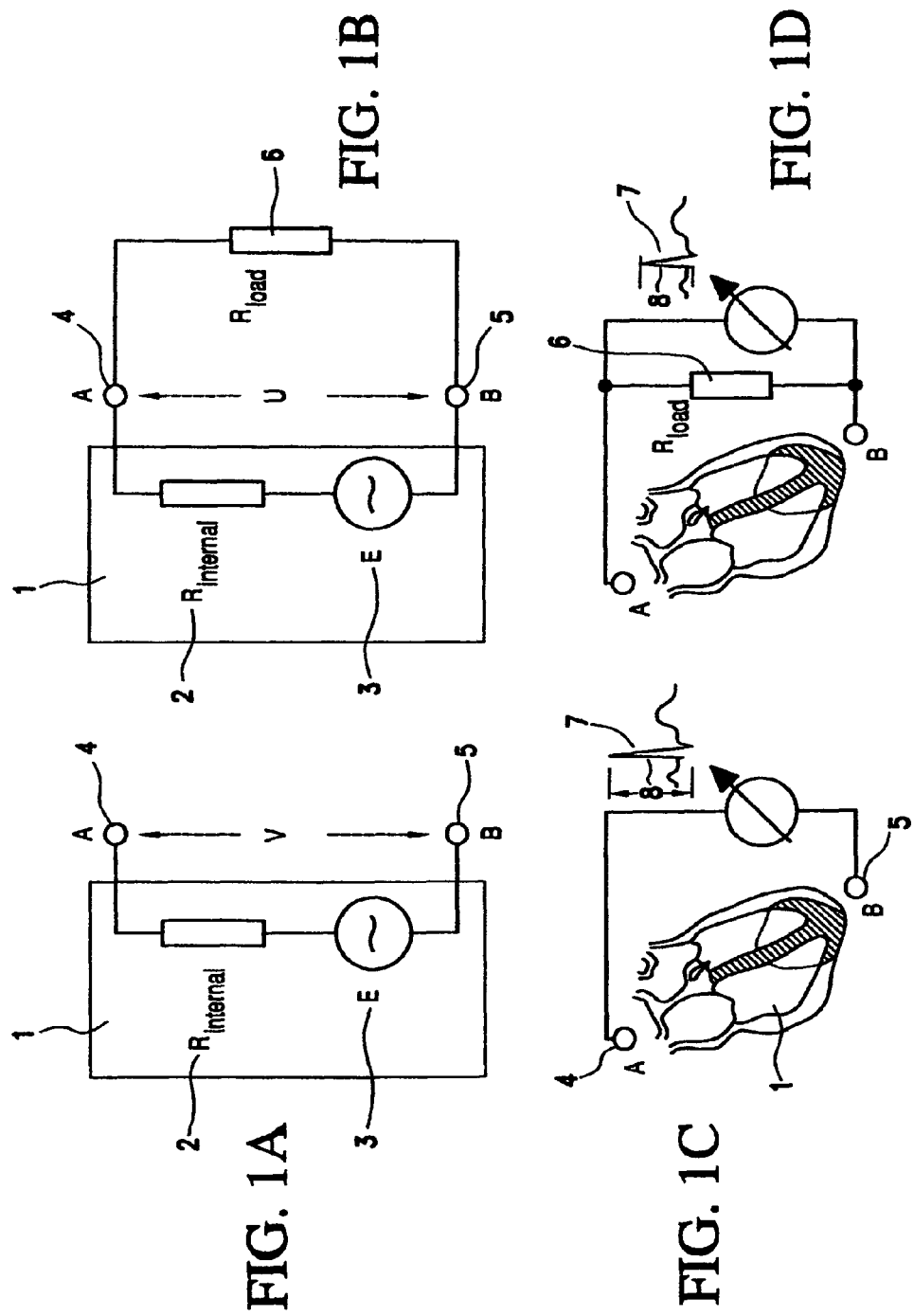

$R_{insp} \neq R_{exp} \longrightarrow U_1 \neq U_2 \longrightarrow U_1 - U_1 = \Delta U_2$
$\Delta$ = respiration

METHOD OF VAGAL STIMULATION TO TREAT PATIENTS SUFFERING FROM CONGESTIVE HEART FAILURE

CROSS-REFERENCE TO RELATED APPLICATIONS

This application is a continuation-in-part of Ser. No. 12/857,140, now U.S. Pat. No. 8,219,198, filed Aug. 16, 2010, which is a continuation of Ser. No. 11/104,389, now U.S. Pat. No. 7,778,709, filed Apr. 11, 2005, which is a continuation-in-part of Ser. No. 10/622,184 filed Jul. 16, 2003, which is a continuation-in-part of Ser. No. 10/155,771, now U.S. Pat. No. 6,829,503, filed May 25, 2002 that claims priority of German patent 10148440-2 filed Oct. 1, 2001 of the same applicant, each of which applications is incorporated by reference in its entirety herein. Applicant claims priority of the aforesaid applications with respect to common subject matter.

BACKGROUND OF THE INVENTION

The present invention relates generally to an improved method of treating a patient diagnosed with congestive heart failure (CHF) or, as the disorder is often termed, chronic heart failure, by stimulating the patient's vagus nerve with a pattern and rate of stimulating pulses controlled by a thoracic impedance derived solely from cardiac signals generated by electrical energy of the patient's heart as the heart is undergoing its cardiac cycle. The invention encompasses evaluation of progression of CHF of the particular patient of interest, and treating the patient by vagal stimulation (VS) from an implanted neurostimulator whose output is controlled according to the impedance and ventilation of the patient to appropriately adjust the patient's heart rate in a correlated manner so as to alleviate the CHF.

Specific resistance of biological materials and impedance measurements have played a major role in modern medicine. The electrical conductivity and capacity of disperse systems have been described as early as 1931 (Fricke et al., *The Electric Conductivity of and Capacity of Dispersed Systems*; Physics 1931; 1:106-115). Later, especially in the 1950s and 1960s, significant interest was directed towards the resistance of biological materials (e.g., Geddes L. et al., *The Specific Resistance of Biological Material: A Compendium of Data for the Biomedical Engineer and Physiologist*, Medical and Biological Engineering 1967, 5:271-293). The application of impedance and resistance measurements for cardio-circulatory function by measuring the blood and body temperature has been studied extensively by Geddes et al., Medical and Biological Engineering 1967, 11:336-339). Also, internal and external whole body impedance measurements have been used for noninvasive monitoring and determination of cardiac output (Carter et al., Chest 2004, 125:1431-1440). In addition, the feasibility of using intracardiac impedance measurements has been evaluated by E. Alt et al. for capture detection in connection with cardiac pacing (Pace 1992, 15:1873-1879).

Background patents that describe the use of impedance in conjunction with implantable devices are referenced in U.S. Pat. No. 5,003,976 to Alt, which describes the cardiac and pulmonary physiological analysis via intracardiac measurements with a single sensor. The '976 patent discloses that a single functional parameter, namely intracardiac impedance, varies both with the intrathoracic pressure fluctuations following respirations and with cardiac contraction. This value is representative of both pulmonary activity and cardiac activity. The finding indicates that this information derived from intracardiac impedance can be used not only to monitor the patient's cardiac and pulmonary activity, condition and cardio-circulatory status, but also, to control the variability of the rate of an implantable cardiac pacemaker.

U.S. Pat. No. 4,884,576 to Alt et al. discloses a self-adjusting rate responsive cardiac pacemaker and method based on the intracardiac signal derived from impedance measurements using an electrode implanted into the heart. And U.S. Pat. No. 4,919,136, also to Alt, describes a ventilation controlled pacemaker which uses the ventilation signal derived from those impedance measurements with an electrode in the heart to adjust the pacing rate.

Recently, considerable interest has been focused on the monitoring of congestive heart failure by means of impedance. U.S. Pat. No. 6,473,640 to Erlebacher describes a system that detects changes in resistance to a flow of current in the systemic venous system, and detects changes in impedance to a flow of current through lungs. The specific signal processing enables a determination of congestion in the venous or in the pulmonary system by application of differential signal processing of impedance. Other methods, such as are described by Combs in U.S. Pat. No. 5,957,861 and Riff in U.S. Pat. No. 5,876,353, respectively pertain to impedance monitoring for discerning edema through evaluation of respiratory rate, and use of implantable medical devices for measuring time varying physiological conditions, especially edema, and for responding thereto.

U.S. Pat. No. 6,104,949 to Pitts-Crick relates to a device and a method used for the diagnosis and treatment of congestive heart failure. Godie, in U.S. Pat. No. 6,351,667, describes an apparatus for detecting pericardial effusion, in which a wire probe anchored to the right heart ventricle and two other wire probes are used to measure the impedance between the different probes in order to assess the degree of pericardial effusion.

U.S. Pat. No. 4,899,758 to Finklestein et al describes a method and apparatus for monitoring and diagnosing hypertension and congestive heart failure. U.S. Pat. No. 6,336,903 to Brody relates to an automatic system and method for diagnosing and monitoring congestive heart failure and the outcomes thereof. U.S. patent publication 2002-0115939 to Moligan et al describes an implantable medical device for monitoring congestive heart failure in which incremental changes in parameter data over time provide insight to the patient's heart failure state.

The measurement of heart failure becomes of greater clinical interest and importance as more than 5 million patients in the U.S. are affected. With deterioration of myocardial function, patients often require repeated hospitalization. Current methods of monitoring congestive heart failure cannot reliably predict an early occurrence of this congestive heart failure; but an understanding of its occurrence may provide an early indicator of this adverse event for the patient.

A considerable number of new treatment forms have been introduced into clinical practice. It had been shown that congestive heart failure can be treated, not only by drugs, especially Beta blockers, but also by biventricular pacing. This method makes use of the exact timing of a stimulus, not only to the right ventricle or to the septum, but also to the left side of the heart by means of an electrode which is implanted into the coronary venous circulation. By these means, the left ventricle can be stimulated at a time that provides an optimal synchronization of the heart and improves the mechanical effectiveness of the systole by synchronizing the depolarization of the right heart, the septum and the left heart. This avoids the ineffective late contraction of the left ventricle at a time when the septum depolarization has already occurred, and the squeezing of the blood by synchronous action of the septum and left ventricle is no longer present. In addition, the reduction in mitral valve regurgitation by this type of resynchronization has been shown.

Studies published at the 2005 meeting of the American College of Cardiology in Orlando, Fla., USA (CARE-HF study) illustrate that not only the quality of life of those patients with New York Heart Association, Heart Failure Class 3 and 4 can be improved, but also the life expectancy. This recent data show very impressively that over a 3-year period such biventricular stimulation and the mortality can be reduced by half in a highly significant manner. All these new devices improve the survival and quality of life of patients and have a beneficial effect on re-hospitalization. Nevertheless, the occurrence of heart failure is still a major problem for these patients, and it is beneficial to detect such a heart failure as early as practicable.

Accurate adjustment of heart rate also plays a major role in patients with implantable devices, such as pacemakers and defibrillators. Rate adaptive pacemakers in the past have provided an open type of correlation between a signal parameter to adjust the heart rate and the affected heart rate. However, even multiple sensor parameters that have been used for adjustment of the pacing rate have not brought the real need of a patient to clinical practice, mainly a closed-loop monitoring of heart rate.

In the healthy person, the heart rate is regulated by a very sophisticated closed loop and negative feedback. Heart rate only increases to a level with exercise which is physiologically beneficial. This means that if a patient exercises only mildly, his heart rate increases proportional to the increase in oxygen uptake for this person which is a fraction of his maximum exercise capacity, maximum oxygen uptake and aerobic and anaerobic capacity. Thus, if someone is well-trained, an external load of 50 watts might represent only 25% of his/her maximum exercise capacity if the patient is capable of exercising up to a level of 200 watts. With this external load of 50 watt the heart rate will increase by only the fraction that is represented by the patient's resting heart rate and maximum exercise heart rate. In other words, such a well-trained person will increase his/her heart rate only by 30-35 beats per minute (bpm). A less capable patient who has a maximum exercise capacity of 100 watts, will increase his/her heart rate with the same external load to a higher degree. In that case, the slope of increase in heart rate depends not only on a fixed relation of a sensor parameter, such as ventilation or physical activity or any other physiologic parameter having a suitable correlation with heart rate, but also on his/her underlying cardio-pulmonary exercise capacity and condition.

According to Motonori Ando et al (Circulation 2005; 112: 164-170), stimulation of the vagus nerve can exert antiarrythmogenic effects during acute myocardial ischemia. While the Ando paper refers to studies conducted on rats, the authors postulate that human patients may benefit from such effects of vagal stimulation, which are accompanied by prevention of the loss of phosphorylated Cx43 during acute myocardial ischemia. Cx43 is a subtype of connexins Cx, highly homologous proteins which compose gap-channel junctions that have been implicated in the electrical coupling of excitable tissues, such as cardiac muscles. Cx40 is a second subtype of connexins in the adult heart muscle but is primarily found in atrial tissue, whereas Cx43 is predominantly expressed in ventricular tissue.

According to other studies cited by Ando et al in their paper, the protein content of ventricular Cx43 is remarkably reduced in ischemia and heart failure, and this reduced expression of Cx43 increases the incidence of ventricular tachyarrythmias and reduces the conduction velocity during acute myocardial ischemia. These results, they say, suggest that the loss or dysfunction of Cx43 in cardiomyocytes may be one of the mechanisms that promote lethal ventricular tachyarrythmias, including ventricular fibrillation.

Studies reported prior to that of Ando et al demonstrated that ventricular arrhythmia is one of the major causes of death in chronic or congestive heart failure. It is reported that VS therapy markedly improved long term survival in an animal model of chronic heart failure after myocardial infarction (see, e.g., Meihua Li et al, "Vagal nerve stimulation markedly improves long-term survival after chronic heart failure in rats," Circulation 2003; 109: 120-124; and Correspondence in the same publication concerning a query raised by Springer et al on the latter study as to whether VS provides an anti-inflammatory intervention in CHF, and response thereto by Li et al, op. cit.; e34).

While the mechanisms of VS on myocardial infarction are not known, Ando et al postulate that the antiarrhythmogenic effects and accompanying prevention of the loss of Cx43 exerted by VS during acute myocardial ischemia play a critical role in improving ischemia-induced cellular electrical instability of ventricular myocytes. VS has also been postulated to contribute to an antifibrillatory effect.

In U.S. Pat. No. 6,622,041 ("the '041 patent"), incorporated by reference in its entirety herein, Terry et al describe a method of treating CHF and autonomic cardiovascular drive disorders, in which an implanted neurostimulator is used to apply stimulating electrical pulses in a predetermined pattern and rate to the patient's vagus nerve at or above the cardiac branch of the nerve. The neurostimulator is designed to sense the patient's heart rate from an electrode or array engaging or proximate the nerve as the basis for controlling the vagal stimulation. The stimulating pulse rate is varied according to the physical status of the patient, that is, at rest or engaged in physical exertion, albeit moderate, so as to respectively reduce or increase the patient's heart rate relative to the normal resting rate. The physical state of the patient in this respect is detected by a metabolic need sensor, such as an accelerometer, which may be housed within the same case as, and operatively coupled to the neurostimulator. Terry et al hypothesize that this VS treatment can reduce the occurrence and the symptoms of heart failure and improve the cardiac output of the heart.

Terry et al refer to studies reported by Klamath (Pace 1992; 15: 1581-1587) on the neurocardiac responses to vagoafferent electrostimulation in patients for the control of epilepsy, which indicated that stimulation of the vagus nerve below the superior cardiac branch can have a long term beneficial effect on the balance of the sympathetic/parasympathetic system, and serve to demonstrate the feasibility of using vagus nerve stimulation to provide the heart with adequate parasympathetic support to promote natural healing.

The '041 patent describes stimulating the vagus nerve either above its cardiac branch or at the cardiac branch at a rate determined to limit the upper heart rate of the patient to a physiologically safe limit. Vagal stimulation below the cardiac branch will not affect heart rate to the same extent. The cervical cardiac branch of the vagus nerve provides the most convenient access location for attaching the stimulating electrode because of where the branch from the main trunk of the vagus is located in the patient's neck, providing a desirably long section in the neck from which to select a site for electrode attachment.

The vagal stimulation pulse frequency or rate at the site has an inverse effect on the heart rate, and may be experimentally determined and appropriately adjusted to achieve a particular heart rate for each patient during a treadmill test. Terry et al stress the need for each of the VS rates to be verified by the patient's attending physician to assure the propriety of a prescribed target heart rate for that patient.

As an example cited in the '041 patent, stimulation may be commenced whenever the heart rate exceeds a predetermined threshold, such as 90 BPM. Alternatively, the stimulation rate may be adjusted automatically to maintain the heart rate within a specified range. Another alternative specified in the '041 patent is to synchronize the vagal stimulation to the P or R wave of the patient's EKG, and deliver a burst delayed from the synchronizing signal. The right vagus nerve is preferred for stimulation because it is more responsive to synchronized heart pacing, but the left vagus nerve may be used instead. The burst duration is approximately 100 msec. The stimulation rate, burst duration, and delay from the synchronization point is programmed to limit the heart rate within a desired range; for example, 60 to 150 BPM. An exemplary VS pulse burst is delivered with a delay of 100 msec from the P wave. Heart rate should be monitored and burst mode parameters, specifically burst frequency, should be adjusted automatically to protect the patient from patterns which could produce a heart rate lower than a physiologically safe level.

Left or right cardiac vagal stimulation at a predetermined rate selected to lower the resting heart rate by a specified percentage, such as 10%-45%, is contemplated to allow more time for the heart muscle to repair during muscle contractions, according to Terry et al. It is also contemplated to be beneficial in stimulating the growth of additional coronary capillaries, so as to supply more blood to the heart muscle, and may also be beneficial in dilating the coronary vessels further increasing coronary blood flow, to aid in recovery and strengthening of the heart muscle. When a metabolic need for increased heart rate is indicated in the neurostimulator of the '041 patent, the device programming causes VS cessation or sufficient reduction so that the patient's intrinsic heart rate may increase, but not exceed an upper rate limit.

In the '041 patent, the metabolic need sensor is adapted to inhibit or control the VS rate to produce a target heart rate within the physician-prescribed limits.

The disclosure of the aforesaid related co-pending U.S. patent application Ser. No. 12/857,140 ("the '140 patent application") pertains to sensing cardiac signals generated by electrical energy of the heart of a patient of interest, applying the sensed cardiac signals as the sole input to signal detection circuitry and from which a factor or parameter related to thoracic impedance of the patient is derived, and to changes in the thoracic impedance, as an indication of the status of a physical condition of the patient and, if present, an abnormality thereof.

Reported attempts to determine impedance measurements from internal signals in the body prior to the '140 patent application had used external power sources to stimulate the heart or to provide currents through the thorax, sensed the resulting cardiac signals or current amplitudes in the thorax, and applied them to detection devices for monitoring and measuring impedance. This external energy could be applied either outside the thorax from a supply external to the body, or by an implantable device that uses energy from a battery housed within the device itself.

SUMMARY OF THE INVENTION

It is a principal aim of the present invention to provide a method of deriving a factor or parameter indicative of the thoracic impedance of a CHF patient from which to evaluate the status of cardiac congestion and of ventilation of the patient and to adjust the vagal stimulation pulse pattern and rate accordingly, so as to obtain the beneficial effects of vagal stimulation on the CHF, and to slow progression of the disorder.

According to the present invention, a method is provided for obtaining or deriving a thoracic impedance parameter from EKG (cardiac) signals of a patient diagnosed with congestive heart failure, for assessing the patient's ventilation and the status of congestion and delivering treatment accordingly. The derivation of impedance, and patient ventilation, is obtained solely from cardiac signals generated by electrical energy of the patient's heart as the heart is undergoing its cardiac cycle, without any artificial excitation from sources external to the heart. Therapy delivered in response involves stimulating the patient's vagus nerve with electrical pulses in a pattern and at a rate controlled by the determined impedance and ventilation, so as to adjust the patient's heart rate with the goal of alleviating the congestive heart failure.

This method is in contrast to the method of the '041 patent, which relies on sensing and using the patient's heart rate to control vagal stimulation. The method of the present invention may be carried out using either open loop or closed loop circuitry.

According to an aspect of the present invention, since the detected impedance varies with patient ventilation, and therefore with states of exercise as well as rest of the patient; a separate metabolic need sensor (as is required by the '041 patent) is unnecessary for purposes of the prescribed therapy. To provide greater accuracy, the relationship between detected impedance and VS output pulse rate for rest and exercise states should be programmed to accommodate the individual characteristic physical condition (specifically; the assessed status of CHF) of the particular patient.

It is therefore another important aim of the invention to provide a system that uses an impedance derived parameter, such as ventilation or the amount of congestion within the thorax, to optimize the response of a vagal stimulator to the status of patient activity, including intensity thereof, as well as the status of rest, for purposes of treating the patient's CHF.

The impedance determination (and concomitant changes in impedance over a predetermined time interval) also serve to provide a strong indication of the status of the heart in its cardiac cycle, from which the extent of progression of the CHF may be determined, and the manner in which an optimum reduction in CHF progression under the circumstances exhibited by the individual patient can be achieved.

Preferably, the cardiac signals are sensed by means in close proximity to the vagus nerve itself, such as by using two electrodes that engage the vagus nerve and that are used as well for stimulation, or through two electrodes that engage the vagus nerve and the case (the "can" or housing of the stimulator) as a third pole, or through the case alone and respective surface-mounted electrodes on the case, electrodes on the header or a combination of different electrode points on the case, on the header and/or on the electrode or lead body. Other vagus nerve cardiac signal sensing electrode arrangements and arrays are disclosed, for example, in U.S. Pat. No. 5,928,272 of Adkins et al ("the '272 patent"), the relevant portion of which is incorporated herein by reference.

BRIEF DESCRIPTION OF THE DRAWINGS

The above and other aims, objectives, aspects, features and advantages of the invention will be better understood from a consideration of the following detailed description of the best mode contemplated for practicing the invention, taken with reference to certain preferred implementations and methods, and the accompanying drawings in which:

FIG. 1A-1D are schematic diagrams of an electrical circuit or system in which a patient's heart is represented by an internal resistance, useful for explaining the basic principles of the '140 application invention;

Figure 2B:
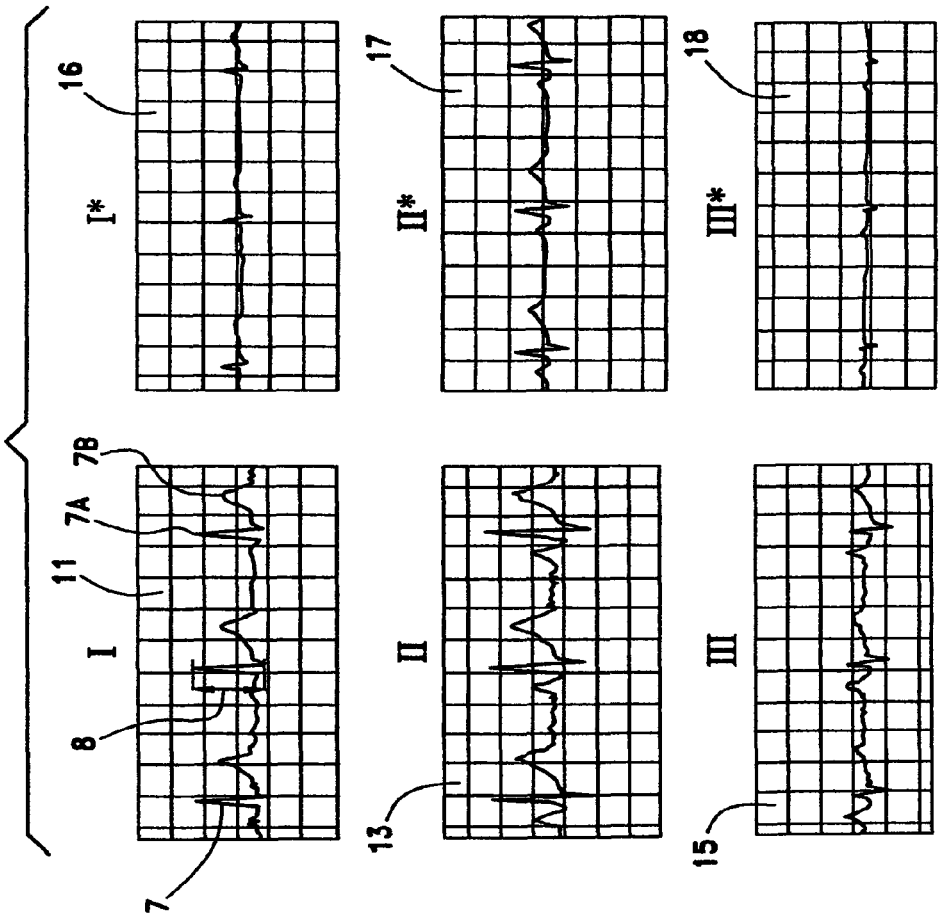
FIG. 2 applies the concepts discussed with reference to FIG. 1, to the principle of different EKG vectors, FIG. 2A illustrating EKG vectors measured for a patient, and FIG. 2B illustrating the EKG tracings for different placements of EKG electrodes.

DETAILED DESCRIPTION OF THE PRESENTLY CONTEMPLATED BEST MODE OF PRACTICING THE INVENTION

As is known, a patient's EKG can be derived from the skin surface of the patient, and represents a voltage (a cardiac signal) generated by the heart. This voltage may be derived by means of electrodes which are adhered to the skin of the patient. Use may be made of different leads, with bipolar electrodes for example between the right arm and the left arm, in the way that the resulting voltage change between these two electrodes represents the main vector of the heart in projection to those leads. Therefore, the amplitude is a measurement of the voltage generated by the heart and the vector. The input impedance of an external EKG machine is standard in a range between 1-10 megohms. This means that the input impedance and resistance of such an amplifier is very high and therefore no current is shunting through the machine and the voltage always represents the maximum voltage generated from the energy source, namely the heart. Differences in voltages with the current EKG measurement result from different vectors that project two different leads on the surface of a patient.

The same holds true for voltages detected with implantable devices from leads that are situated within the heart or within the thorax or even implantable devices that have EKG electrodes outside the thorax, such as EKG loop recorders or devices that are suitable for monitoring the EKG and congestive heart failure from electrodes that are situated outside the thoracic cage as described by Alt et al in the aforementioned related patent application U.S. Ser. No. 10/155,771.

The underlying principle may be summarized, for exemplary purposes, from experiments conducted by the applicants. The measurements that resulted from placement of standard EKG I, II, and III leads on the patient were recorded in the presence and absence of an external load. The amplitude of the EKG signal that corresponds to the measured voltage is a function of the impedance of the EKG amplifier.

The theory is that the heart acts as a battery. A battery fails when its internal resistance has increased to a level at which the battery can no longer supply a useful amount of power to an external load. That same principle applies to the measurement of electrical energy generated by the heart. That is, if several loads are applied to the measurement device, which may be an implantable cardiac pacemaker, a defibrillator, a device for monitoring the occurrence of heart failure, or a diagnostic device for monitoring the physical condition of a patient, the same phenomena can be used to calculate the internal impedance at the site of measurement. Preferably, the calculation or determination is of the thoracic (and preferably, intrathoracic) impedance or of local impedance and/or its relative changes with time for a given patient.

According to an important aspect of the disclosure of the '140 patent, a method of evaluating the cardio-circulatory condition of a patient includes determining the patient's thoracic impedance based on information from cardiac signals derived solely from electrical energy generated by the patient's own heart and delivered as the sole input to signal monitoring or detection circuitry. The intrathoracic impedance information may be used, for example, to optimize the rate response of a rate adaptive pacemaker, or, as in the present invention, to optimize monitoring, evaluating and treating a patient's congestive heart failure. Another aspect of the '140 patent disclosure involves a method of adjusting the heart rate of a patient by means of an implanted rate adaptive pacemaker, where automatic adjustment of the pacing rate of the pacemaker is achieved in response to a determination of the patient's intrinsic impedance in this manner. The patient's intrinsic impedance information may be used instantaneously to influence the rate adaptation on a continuous or ongoing basis within minutes. Alternatively, the rate and cardio-pulmonary response derived from the intrinsic impedance may be applied to determine the rate adaptation on a longer term basis, such as on a daily or monthly basis.

For example, the device may be implanted subcutaneously to monitor the patient's EKG, and to detect changes in the thoracic impedance based on differential signal processing of the EKG. Then, information concerning the impedance changes may be applied within the device to determine the cardio-pulmonary status of the patient. In circumstances where the patient is suffering from heart failure, the device is adapted to monitor the patient's heart failure by performing the determination of impedance and processing thereof using cardiac signals sensed from the electrical energy generated by the patient's own heart as it undergoes its cardiac cycle in the absence of application of electrical energy to the heart from another source, and applying those cardiac signals as the sole input to signal processing circuitry of the device.

Information about the cardiac function of the patient may be obtained using a method in which electrical signal information from an EKG derived from depolarization and repolarization of the patient's heart, representing systole and diastole, accordingly for different phases of the heart represented by the EKG, is continuously processed using as its basis, the electrical signals generated by the patient's own heart. On the other hand, the impedance of the patient's heart may be analyzed with systole from a point close to the T-Wave of the EKG signal, and information on the diastolic status of the heart may be derived from an impedance signal at the R-Wave of the EKG signal. Then, a comparison between systole and diastole may be used to ascertain indirectly cardiac stroke volume and the cardio-pulmonary status of the patient.

Similarly, the function of a body-implantable defibrillator may be enhanced by determining the impedance between sensing electrodes of the defibrillator, and determining changes in that impedance, using cardiac signals sensed from the electrical energy generated by the patient's own heart as the sole input to processing circuitry of the device.

A device for evaluating the cardio-circulatory condition of a patient is implemented with means for determining the patient's thoracic impedance and changes in that impedance based on information derived from the electrical energy generated by the patient's heart. And the desired information may be obtained by extremely simple means so that the changes or additions required to achieve these benefits with even currently available devices can be minimal, such as including surface mounted electrodes for monitoring the patient's surface EKG in subcutaneously implanted devices.

Referring to FIGS. 1-13, the basic underlying method and device are described in terms of a diagnostic and/or therapeutic technique to enhance the specificity of a body-implantable device such as an artificial cardiac pacemaker, a rate adaptive pacemaker, a neurostimulator, or a monitoring device for evaluating the cardiopulmonary functional status of the patient.

Throughout the views of the drawings, identical reference numbers indicate identical structures, elements or items. The Figures are not intended to represent the actual or relative sizes of devices, but rather, to provide an understanding of the principles on which the methods and devices are based.

FIGS. 1A-1D are simplified schematic diagrams of an electrical circuit or system in which the heart of a patient 1 is represented by an internal resistance ($R_{internal}$) 2, at least in parts 1A and 1B. In principle, $R_{internal}$ is the sum of many individual resistances or impedances consisting of myocardial tissue, fibrous connective tissue in the heart, pericardium, blood within the heart, fluids within the intracellular spaces, and the surrounding environment of connective tissue atria, pulmonary structures, venous structures, and lung tissue, i.e., the thoracic or intrathoracic impedance. The multiplicity of cells within the heart depolarize, and this depolarization creates an electrical force which threads through the heart with a certain vector. This initial electrical source represented in the circuit schematic of the Figures as a voltage source E (3) has a magnitude that can be measured between electrodes at points A (4) and B (5). The latter two points may constitute the sites of electrodes of an external measuring instrument or EKG amplifier.

Virtually the same voltage as the original source voltage E 3 will be present and remain so, if the impedance between measuring points 4 and 5 has a magnitude of several megohms. This is because under that condition little or no current is flowing between those points. In principle, this maximum voltage is present, for example, at the input amplifier of an implantable pacemaker, since they have an impedance of several hundred kilohms or megohms; and the same is true of other implantable diagnostic or therapeutic devices, such as devices that measure the patient's EKG. For example, external EKG strip chart recorders or EKG monitors have an impedance of 1 megohm or more, thereby allowing them to detect the maximum voltage present between points of the body at which their electrodes are attached or located.

In FIG. 1B the schematic shows a heart 1, in circuit with an internal resistance 2, a source voltage 3 that is detected between electrode points or sites 4 and 5, corresponding to what has been described above for FIG. 1A. However, in this case an additional external resistance of magnitude $R_{Load}$ 6 is connected in circuit between electrode points 4 and 5. If the magnitude of the resistance of load 6 is considerably lower than the input impedance between 4 and 5 represented by, say, the virtual open circuit impedance of an amplifier, discussed for the circuit of FIG. 1A, considerable current will be shunted through this lower resistance. As in the case of a failing battery, then, the initial full voltage E (3) will not be detected since, by Ohm's Law (U=IR), a drop in voltage will be observed with decreased R.

This example is carried forward in FIGS. 1C and 1D. In each of those Figures, the heart 1 generates a certain EKG signal 7 between measuring points 4 and 5, which has a certain amplitude 8. In FIG. 1D, the connection of an input amplifier 8 with a relatively low resistance $R_{Load}$ 6 across points A and B results in an EKG signal 7 having an amplitude considerably lower than that in the case of the much higher, virtually open circuit resistance across A and B in FIG. 1C.

In principle this observation can be compared to a battery. When a battery fails it is typically because its internal resistance has increased to a level that no longer supports the supply of a useful amount of electrical energy to an external load. If one measures the voltage V of a failing battery which is disconnected, it is usually found that the battery has a nearly normal voltage because a conventional voltmeter used to perform the measurement has an input resistance much higher than the internal resistance of the battery. If, however, the failing battery is connected to a low external resistance such as load 6 in FIG. 1B, the terminal voltage U of the battery drops precipitously. This can be interpreted as the battery dropping most if its source voltage across its own internal resistance, so little or no voltage is available for external services. For example, an ideal battery with 0 internal resistance or infinite internal conductance and a voltage E of 12 volts, when supplying power to an external load having a resistance of 1 ohm, will produce a current of I=12 amps and a power of E×I=144 watts. If the battery has an internal resistance of 2 ohm, or an internal conductance as low as 0.5 siemens, then with this load, the terminal voltage U of the battery will drop to 4 volts. The output current of this failing battery will drop to I=U/$R_{Load}$ which is 4 amps, and the output power is 16 watts.

The same principle holds for conventional electrocardiography along the main electrical excitation vector. Since an EKG measurement is detected with high input impedance, this conventional measurement gives no insight into the electrical power of the source, in this case the heart of the patient. Furthermore, the absolute voltage of EKG signals is not a valuable indicator of various pathological situations. Indeed, despite great diversity of cardiac diseases it is common clinical experience that individual variability and the amplitude of the EKG wave as detected from state of the art EKG amplifiers is not indicative of any kind of disease. The voltage of a conventional EKG is reduced only in very few clinical situations when large electrical shunts are present, such as a pericardial effusion which constitutes a large conductor around the heart that shunts the electrical energy with low intrinsic resistance.

The terminal voltage U in FIG. 1B (which represents the R wave amplitude 8, represented in FIG. 1C by QRS-complex 7) should drop by $E-(R_{internal} \times I)$, where $I=U/R_{Load}$. The internal resistance $R_{internal}$ 2 can be calculated by the equation $R_{internal}=(V-U)/(U/R_{Load})$, where V is the voltage between electrode points 4 and 5 which is disconnected from the load in FIG. 1A and U is the terminal voltage between 4 and 5, across which the electrical load $R_{Load}$ 6 is connected. Based on $R_{internal}$, the internal electrical conductance $S_{internal}$ of the heart can also be calculated by the equation:

$$S_{internal}=1/R_{internal}, \text{ in siemens.}$$

Figure 2A:
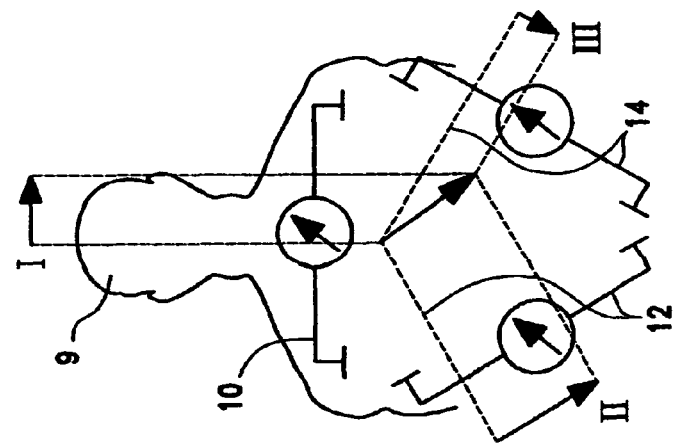

These equations are applied in practice in FIG. 2, according to the principle of different EKG vectors. FIG. 2A represents a patient 9 in which EKG lead I 10 is represented by electrodes to the patient's right and left arms, with voltage measurements shown in EKG tracing 11 (FIG. 2B). Electrode detection lead/electrodes II 12 produces the tracing 13, and the voltage detected between the electrodes of lead III 14 is shown in the tracing 15 for lead III. Tracings 11, 13, and 15, then, represent the EKG signal obtained for the respective vector projections of the leads 10, 12 and 14. If an external load is now connected in parallel with the input impedance of the EKG amplifier, a voltage drop will be observed for the same patient as shown by tracings 16 (for lead I), 17 (for lead II), and 18 (for lead III), because part of the energy delivered from the patient's heart is shunted through the additional external load.

FIG. 3 illustrates various situations in which the internal resistance $R_{internal}$ of the heart is represented not as one single value, but by plural individual impedances. In FIG. 3A, the internal resistance $R_{heart}$ of the heart 19 is represented by the structural resistance of the heart made up of cells, connective tissue, and primarily solids, and a variable component of resistance $R_{inspiration}$ (or $R_{insp}$) 20 is primarily represented by the filling of the heart with blood. Since blood has a specific impedance of roughly 50 ohms per centimeter (cm), while the specific impedance of heart 19 is 400 ohms per cm, there exists a great influence on the total impedance of the heart, because these two components are in parallel. The internal voltage source 3 in FIG. 3A detected between electrode points 4 and 5 represents a voltage $V_1$ (22) that equals primarily E 3 if the input impedance between 4 and 5 is sufficiently high that all of the voltage E drop occurs between 4 and 5.

Figure 3A:
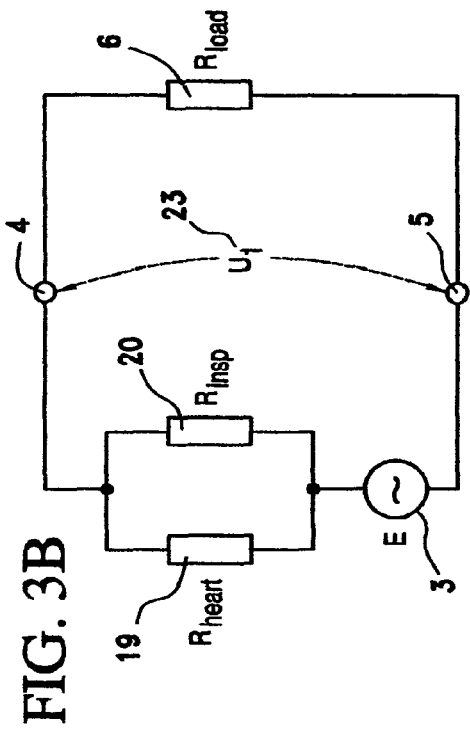
FIG. 3 illustrates various situations in which the internal resistance of a patient's heart is represented in parts A, B, C and D not as one single value, but by plural individual impedances.
Figure 3B:
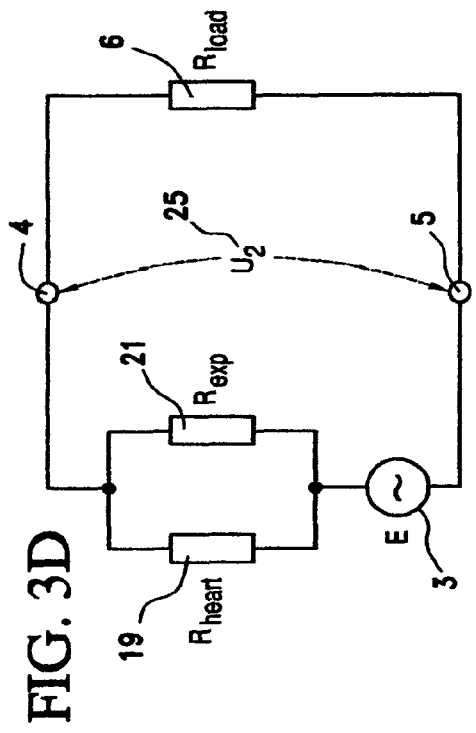
Figure 3C:
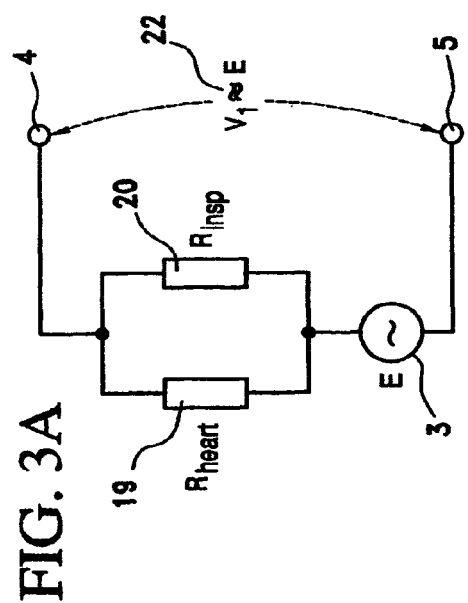
Figure 3D:
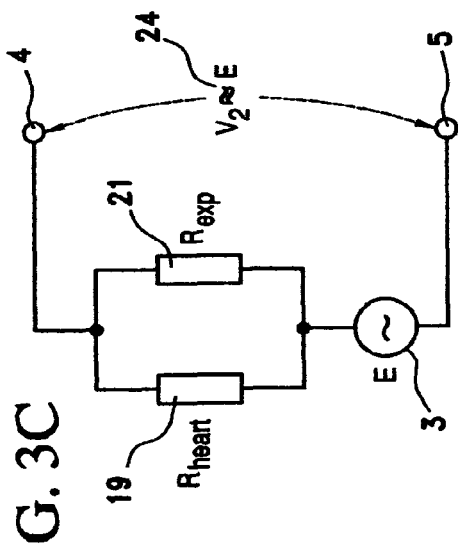

If, however, an additional external load $R_{load}$ 6 of roughly 1 kilohm or less is applied as shown in FIG. 3B, then the voltage between 4 and 5 drops to a voltage U1 (23) which, as earlier described, is lower than the voltage E 22. FIG. 3C illustrates the situation in which a variation now occurs in internal resistance 21, representing the resistance with expiration ($R_{expiration}$ or $R_{exp}$). The total voltage to be detected $V_2$ 24 is now primarily composed of the parallel resistances of $R_{heart}$ 19 and $R_{exp}$ 21. A variation between $R_{insp}$ 20 and $R_{exp}$ 21 will not affect the resulting voltages, $V_2$ 24 or $V_1$ 22, since the input impedance between electrodes 4 and 5 is sufficiently high to avoid further voltage shunting and voltage drop. However, as shown in FIG. 3D, the external load 6 will affect voltage $U_2$ 25 with a variation in internal impedance 21 during expiration, compared to impedance component 20 during inspiration. Thus, if an external load 6 of sufficient load resistance, such as 1 kilohm, is applied to a primarily high input impedance amplifier, variations in internal total resistance build up from $R_{heart}$ 19 and $R_{respiration}$ 20 or 21 have a much greater effect on voltage $U_1$ 23 with inspiration and $U_2$ 25 with expiration. In principle, for this condition it can be said that $R_{inspiration}$ is not identical with $R_{expiration}$ and therefore, $U_1$ 23 is different from $U_2$ 25. It follows that $U_1$ equals the delta of $U_2$, and this represents more or less the impedance factor of respiration, the term "impedance factor" meaning the quotient of impedances 19 and 20 in FIG. 3B compared to the impedances 19 and 21 in FIG. 3D.

Figure 4:
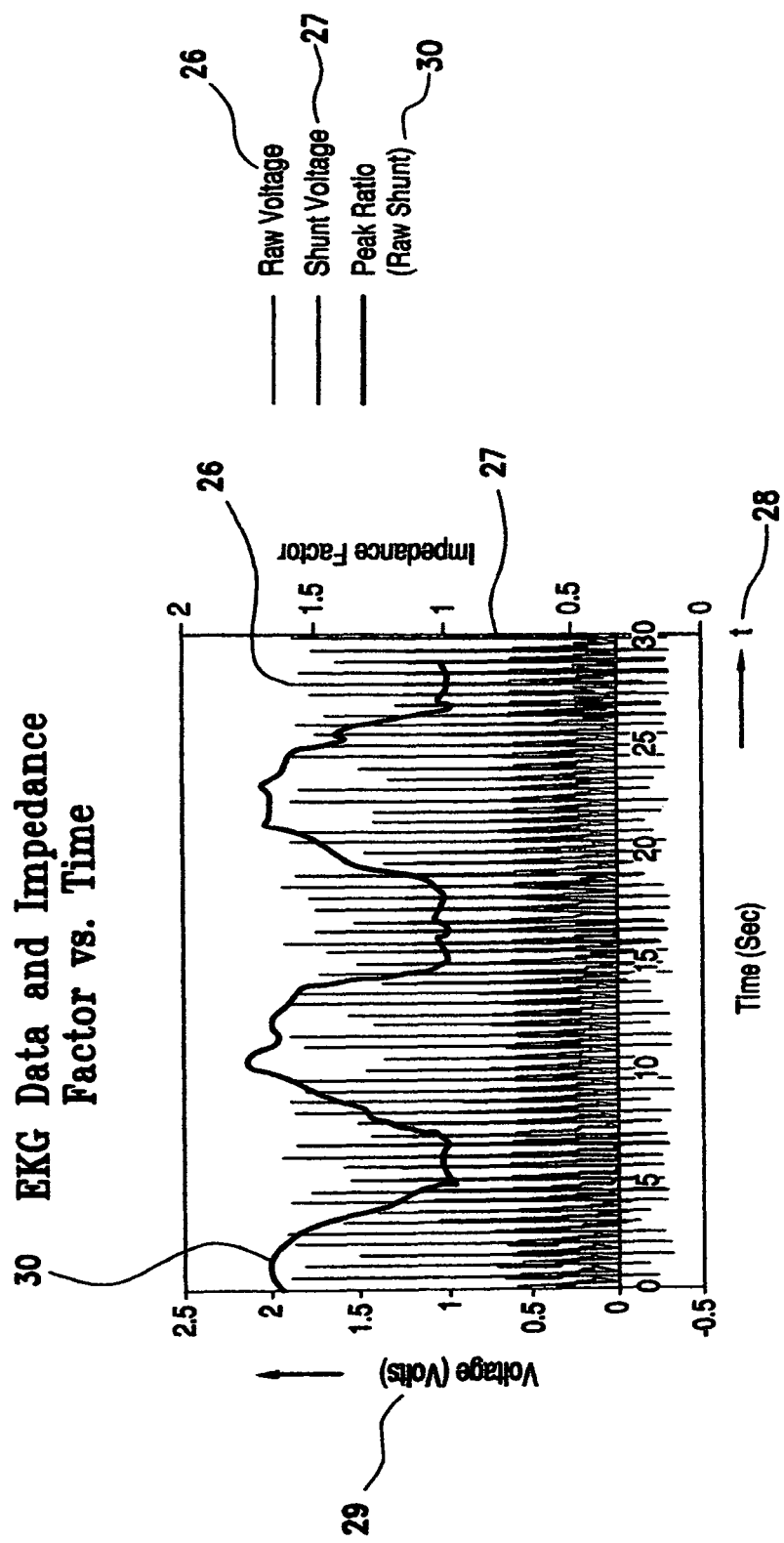
FIG. 4 is a graph of EKG data and impedance factor-versus time that illustrates results from measurements taken with an intracardiac electrode.

FIG. 4 is a graph of EKG data and impedance factor versus time that illustrates results from measurements taken with an intracardiac electrode. A bipolar conventional pacemaker electrode was implanted in the heart and measurements were taken between the electrode tip in connection with the myocardium and a ring located roughly 1 cm behind the electrode tip. These sites can be considered as electrode points 4 and 5 in the Figures described thus far, and a linear high quality amplifier was connected between these two sites. The signal processing was performed in such a way that one signal represented in FIG. 4 as raw voltage 26 represented by the higher bars in the graph was compared to a shunt voltage 27 represented by the smaller bars. To detect the shunt voltage from the same electrode site 4 and 5 by a special program, the input impedance was shunted by a resistance of one kilohm. In FIG. 4 the time axis (abscissa) 28 shows increments of time in seconds and the voltage axis (left ordinate) 29 shows increments of the detected voltage of the two signals raw voltage 26 and shunt voltage 27. The curve 30 represents the quotient between voltage 26 and voltage 27 (i.e., their impedance factor, measured along lines parallel to the right ordinate) or in other words, the quotient of the impedances that change with respiration.

As is clearly seen in the graph, the ratio of the peak signal between raw voltage 26 and shunt voltage 27 represented by curve 30 correlates with the respiration, which was set to 5.5 cycles per minute. The time interval for one respiratory cycle is 11 seconds in this example, which actually represents a ventilation rate of 5.5 cycles per minute.

Various aspects of the continuous EKG signal can be used to derive measurements of impedance factor in FIG. 4, to discern or determine the cardio-pulmonary status of the patient using, in this example, the bipolar conventional pacemaker electrode implanted in the heart for monitoring purposes. Either a continuous line can be averaged if a sufficiently high digitization rate is applied, or, to simplify measurements and procedures, and also to facilitate data handling and power consumption in an implantable device, only certain aspects of the EKG signal need be taken. For example, the latter aspects may be those represented previously herein in EKG signal 7 with amplitude 8, so it is feasible to use only the peak 7A of the R Wave or to take other aspects such as only or additionally the T-Wave peak 7B, of the EKG signal 7 illustrated in FIG. 2B. In the example shown in FIG. 4, the peak of the R-Wave was applied. From the latter Figure, it is clear that considerable variation occurs in the quotient represented by curve 30 (the impedance factor) between inspiration and expiration, which corresponds to the ventilatory cycle rate and its amplitude.

Figure 5:
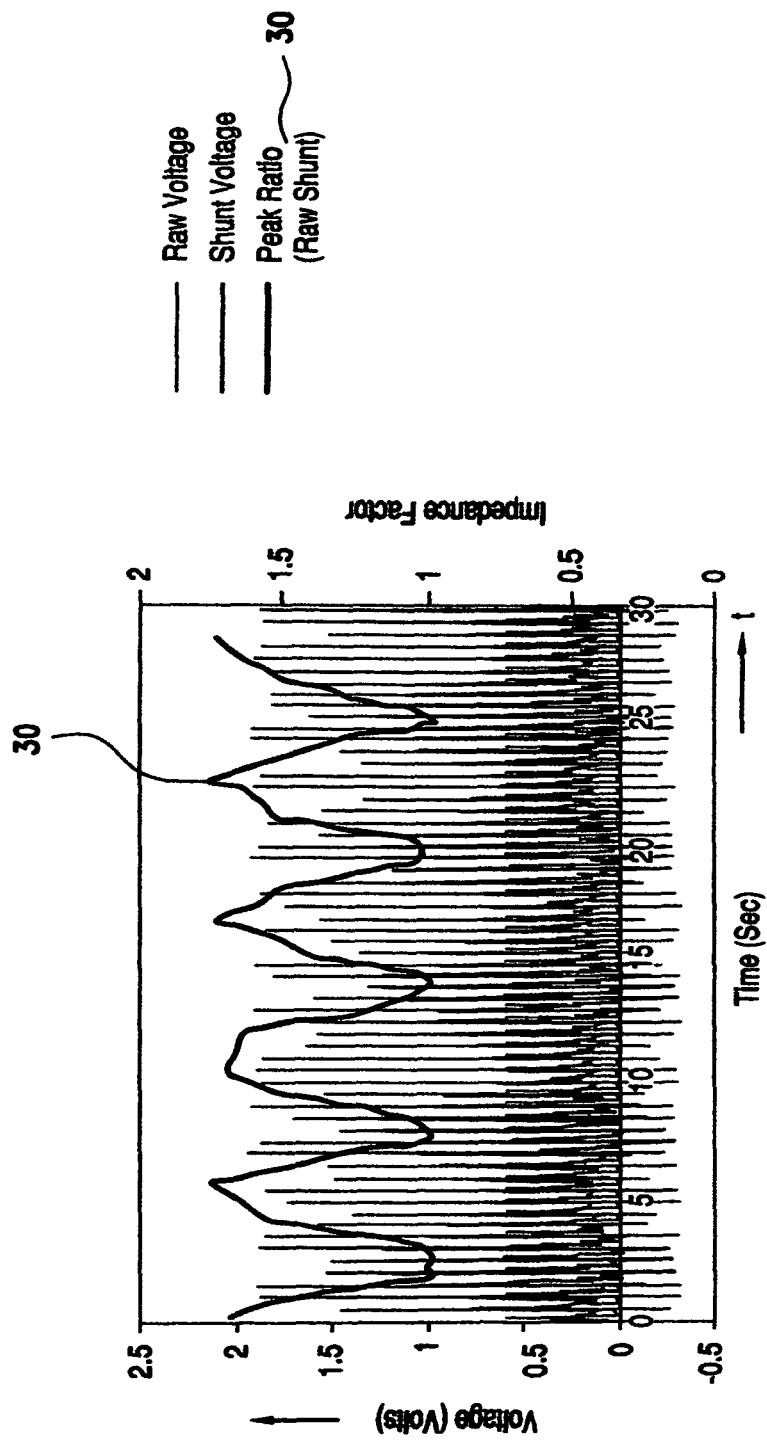
FIGS. 5 and 6 are graphs of EKG data and impedance factor vs. time corresponding to FIG. 4, except for changes (respective increases) in the respiratory rate.
Figure 6:
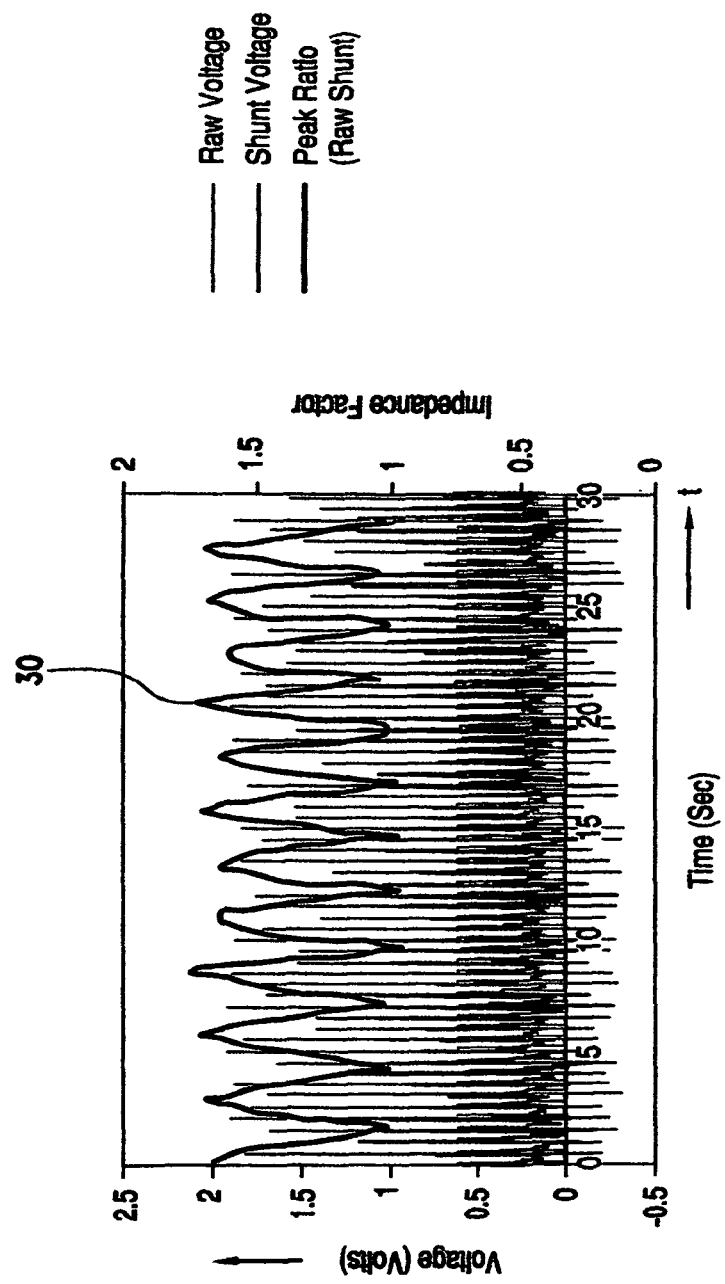

FIGS. 5 and 6 are graphs illustrating the same data setting and the same parameters as in FIG. 4; however, the respiratory rate was changed in FIG. 5 to 10 cycles, and in FIG. 6 to 20 cycles per minute. This change in frequency is clearly shown in the latter two Figures, being represented by peak ratio 30.

Figure 7:
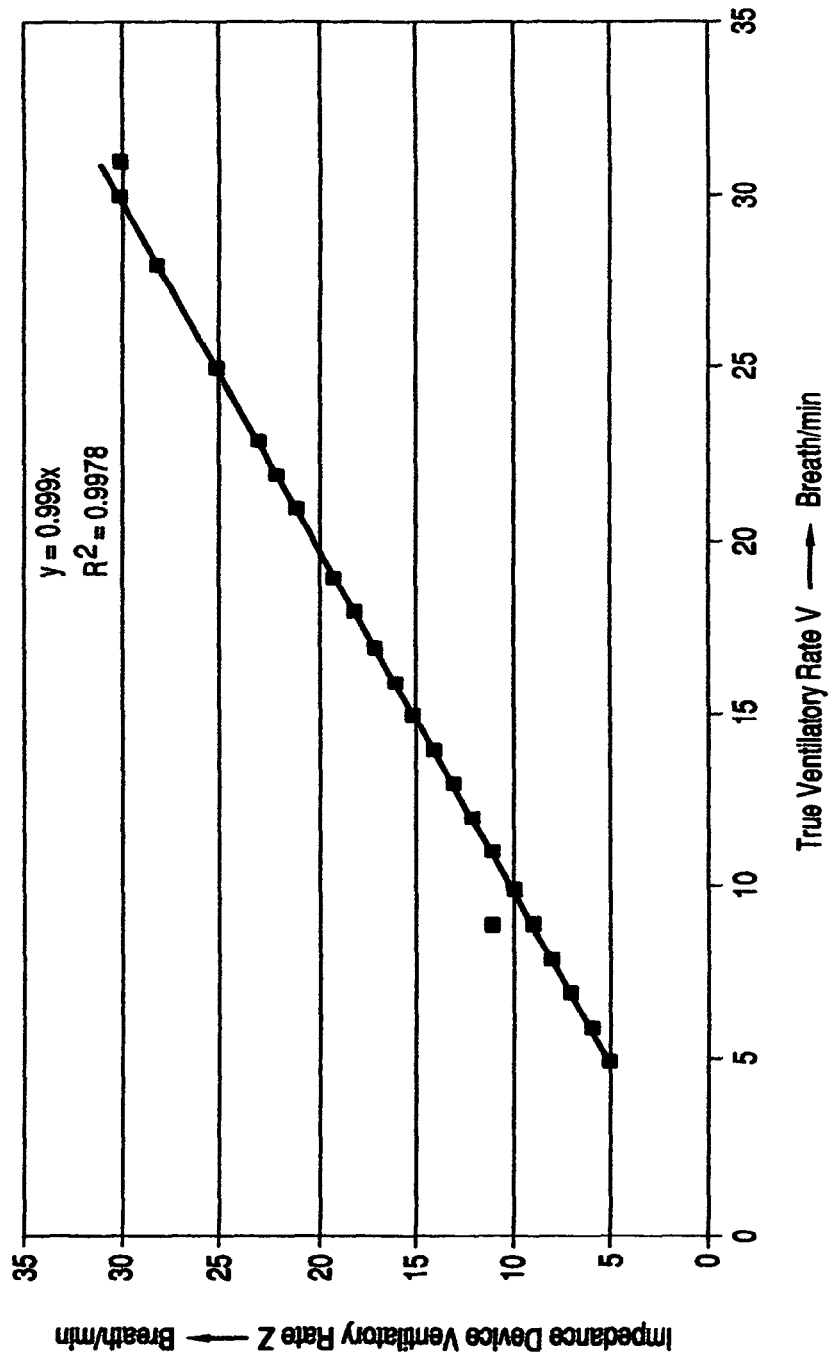
FIG. 7 is a graph that summarizes and compares the measurements of impedance derived ventilatory rate obtained using two different methods.

In the graph of FIG. 7, it is seen that a nearly 1:1 correlation exists between the true ventilatory rate V along the abscissa and the impedance factor (determined in accordance with the methods described earlier herein) derived ventilatory rate Z along the ordinate, for a given patient. This emphasizes that ventilation can be detected, in terms of frequency of breaths, from the impedance derived signal in which the heart serves as the power source for the impedance calculation.

Figure 8:
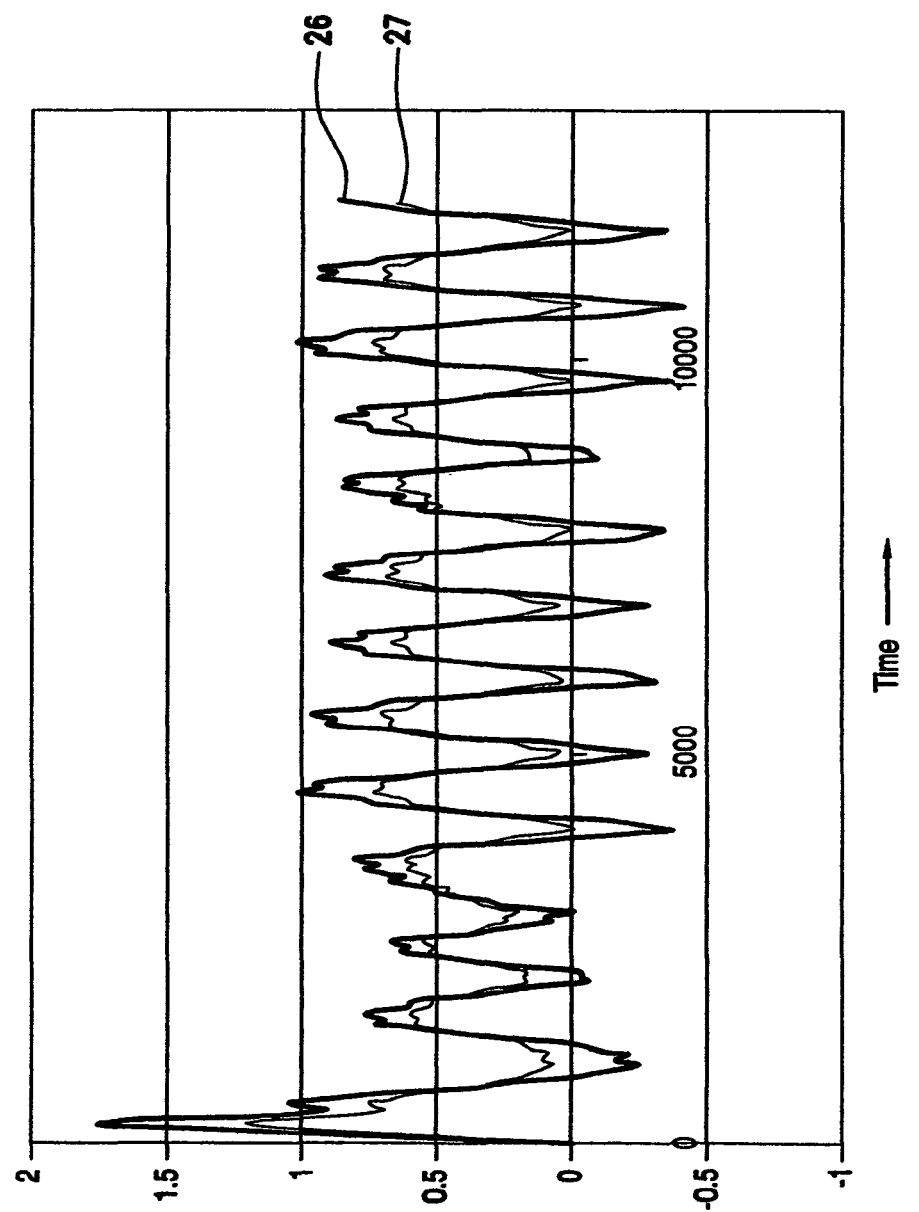
FIG. 8 is a graph that depicts a preferred application of the signal processing means, with relative signal amplitudes over time.

In a preferred application of the signal processing depicted in FIG. 8, the relative signal amplitudes of the raw voltage 26 and the shunt voltage 27 (see FIG. 4 also) are indicated respectively by a higher amplitude and a lower amplitude. Signal 26 was detected from an input impedance exceeding 1 megohm, whereas signal 27 was detected from the reduced shunted input impedance of 0.5 kilohm), both signals having been smoothed by passage through a low pass filter during signal processing. A respiration rate of no more than 50 breaths per minute can be expected for most patients, so a low pass filter of about 1.5 Hz will allow detection of that rate. The difference in amplitude between signals 26 and 27, as well as the respiratory cycle rate, is evident from the Figure.

Figure 9:
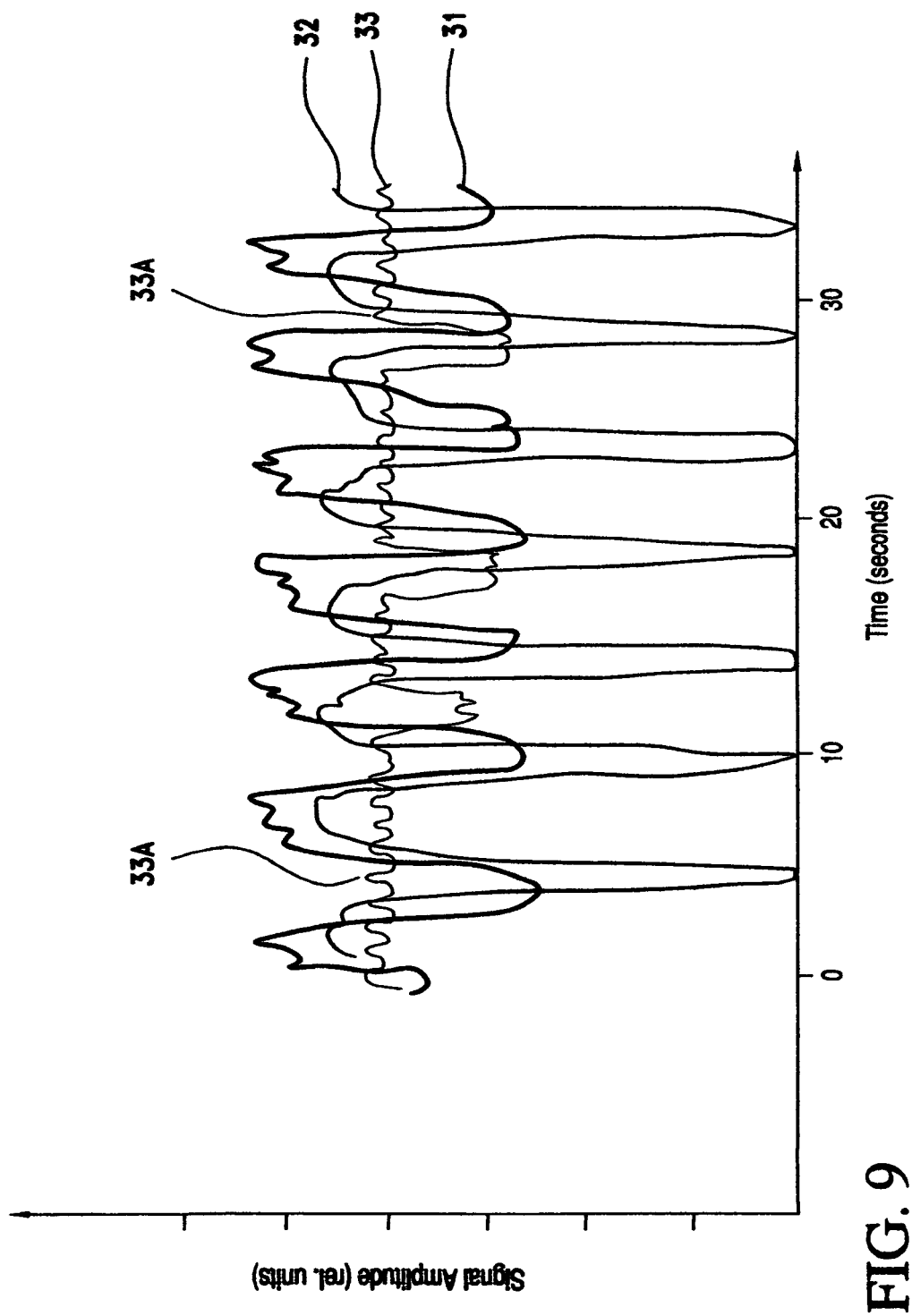
FIG. 9 is a graph that represents the quotient of raw voltage and shunt voltage with different depth and modes of breathing.

FIG. 9 is a graph representing the quotient of raw voltage and shunt voltage with different depths or amplitudes and modes of breathing. The graph illustrates it is feasible to detect respiratory rate, affected by a volume change in the filling of the heart with blood, and also to detect a relative change in amplitude following different tidal volumes. Wave 31 depicts a signal derived from the quotient of high input impedance exceeding 1 megohm and low impedance of 1 kilohm with external artificial ventilation of an individual with a tidal volume of 300 ml per breath. Wave 32 depicts the same for a tidal volume of 850 ml per breath, and wave 33 depicts the impedance quotient with spontaneous breathing at a considerably lower rate. In addition to showing breathing or ventilation, the graph depicts the cardiac component 33A that indirectly reflects stroke volume with systole and diastole. The latter may be obtained, for example, from the observation that depolarization occurs as represented by the peak of the R wave 7A (FIG. 2B) and repolarization occurs at the peak of the T wave 7B, with the mechanical contraction occurring slightly after the peak of the R wave. At that point, the intracardiac impedance (or thoracic impedance) allows determining the extent of filling of the heart with blood, from which to assess the status of congestive heart failure.

Figure 10:
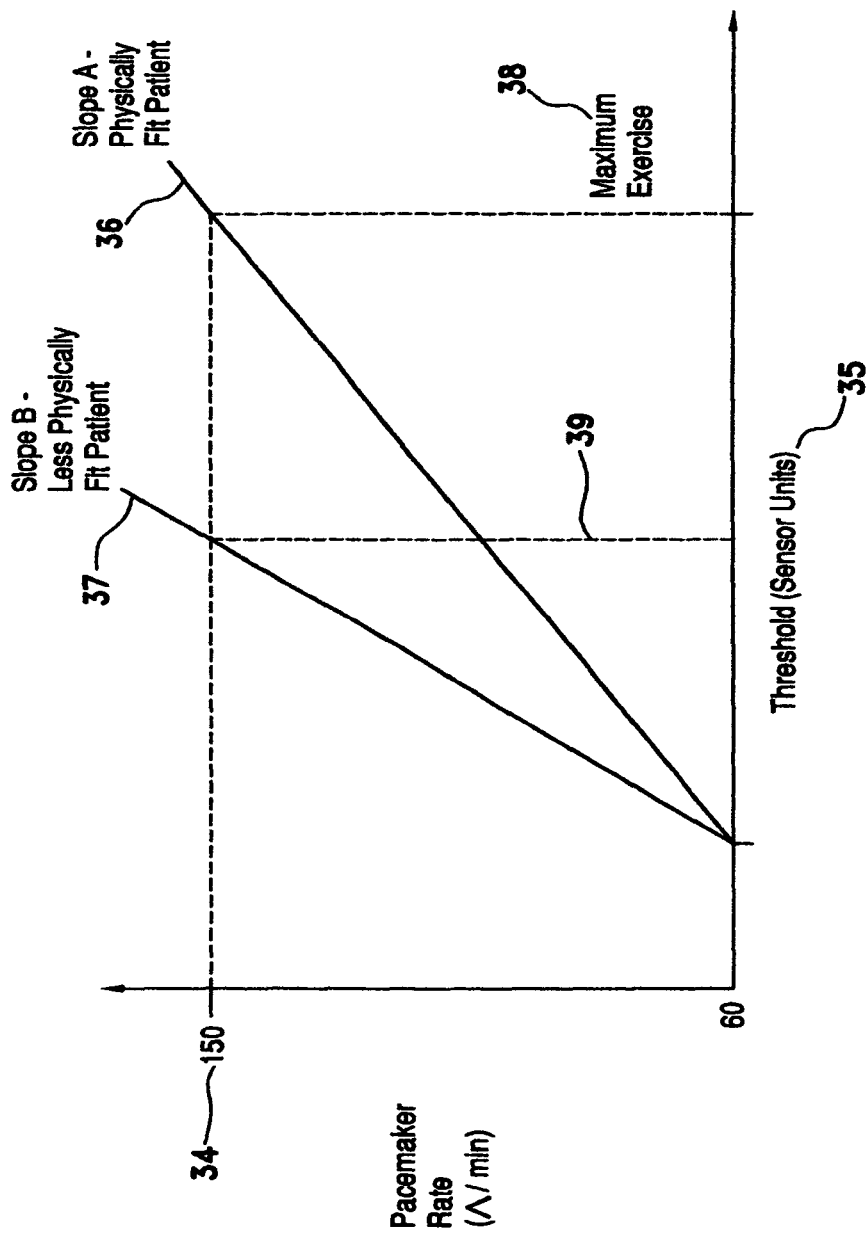
FIG. 10 is a graph that depicts adjustment of rate, in units of pacing rate versus extent of a patient's physical activity detected by a sensor for rate responsive pacing; and useful as well to describe application of the principle to selection and adjustment of vagal stimulation parameters for adjustment of the target heart rate of a CHF patient.

FIG. 10 is a graph useful to show a correlation between rate control for rate adaptive pacing in a pacemaker, defibrillator or other implantable cardioverter device (ICD), and certain principles of the present invention. Units of pacing rate versus extent or intensity of physical activity detected by an activity sensor such as an accelerometer are depicted in the graph. The principle currently used for rate adaptive pacing resides in adjusting the pacing rate of the device implanted in a patient according to the input received from the sensor of patient physical activity. In FIG. 10, change in pacing rate 34 is represented on the vertical axis, the rate increasing from the origin (representing for that axis a preset minimum rate), and units of sensed activity 35 are represented on the horizontal axis with increasing magnitude (intensity of activity) from the origin. Based on empirical assumptions a certain slope function of rate response relative to activity is selected (programmed into the device) by the attending physician, depending on physical fitness (or lack thereof) of the particular patient. Slope A (36) represents a programmed slope function for a physically fit patient, while slope B (37) represents a slope function for a less physically fit patient, recognizing, of course, that "physical fitness" of any degree is a relative term when one is considering a patient who requires artificial cardiac pacing. For any given patient a threshold or limit of maximum pacing rate is set (e.g., 150 bpm, at 34) for empirically determined maximum tolerated exertion 38.

A limitation of prior art open loop systems (which, by definition, lack a feedback parameter) of rate adaptive cardiac pacemakers and other ICDs is that the slope function used for setting an individual heart rate with a given exercise is selected on an empirical basis, and this rate may not be optimum for the situation or condition of a patient from one time to another. The most beneficial rate for the patient with a given exercise might change in a somewhat extreme case from day to day; and for patients with significant coronary heart disease that limits the flow of blood through the coronary arteries and thus may lead to an ischemia, it can be beneficial to limit the maximum heart rate and the slope to a more appropriate value (as at 39 in FIG. 10) than that for a state present even only a short time ago when the myocardial perfusion was different.

An impedance factor or parameter derived in accordance with the present invention can be used to control the individually optimum pacing and heart rate on a closed loop basis, and as well, on a long term trend basis. In closed loop systems previously suggested for rate adaptive pacemakers, hemodynamic parameters have been considered suitable, but a problem is presented in deriving them directly due to their complexity and change. And the added technical difficulty to measure an actual derivative of cardiac output or stroke volume has prevented any significant introduction of those techniques into clinical practice. The relatively minimal energy demand of a system as disclosed herein, can enable control of the effect and adequacy of the pacing rate by means of patient ventilation and/or thoracic impedance factors or parameters derived from the sensed cardiac signal according to the invention.

The present invention applies similar principles of open and closed loop systems for controlling the heart rate of a patient suffering from congestive heart failure, through the delivery of vagal stimulation pulses in a pattern and at a rate or frequency determined by the impedance or ventilation derived factor or parameter. This is to be contrasted with the '041 patent methods, for example, each of which relies on sensing the patient's heart rate during periods or states of patient rest and activity (the latter detected by use of a distinct separate metabolic need sensor), or by reference to the patient's circadian rhythm. In those methods, the sensed rate is utilized to produce what amounts to an "either-or" level one (rest, or sleep interval) or level two (activity, or awake interval) response of vagal stimulation and consequent therapeutic control of heart rate, albeit the transition from level one to level two or vice versa may be programmed to be gradual to avoid rapid change in heart rate. An important distinction is that the level two response is irrespective of changes in the intensity of activity or the progression of the CHF, merely a response occasioned by the occurrence of activity.

Figure 11:
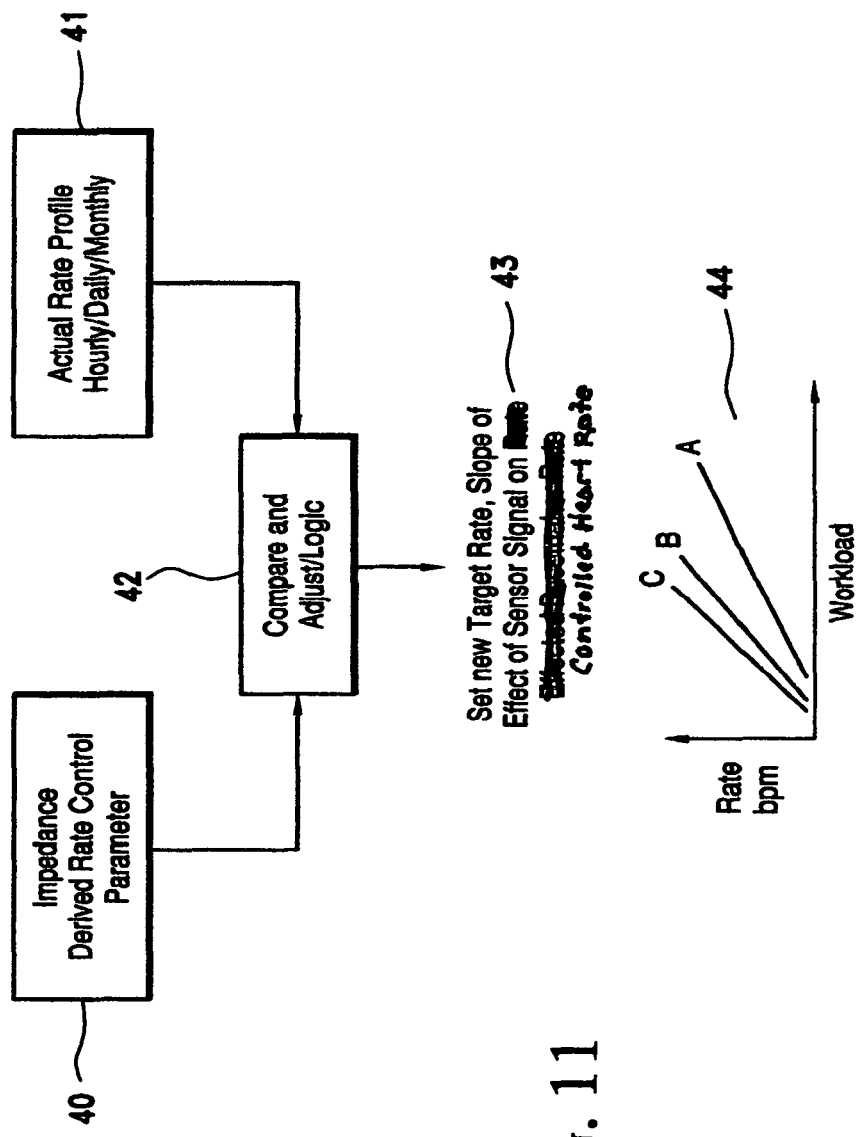
FIG. 11 is a flow chart that shows the principle of a closed loop rate profile optimization for impedance derived parameter control and adjustment of vagal stimulation pattern and rate, and thereby, of the controlled heart rate of a CHF patient while in an active state.

The flow chart of FIG. 11 illustrates how the principle of a closed loop rate profile optimization can be applied to a method of vagal stimulation therapy according to the present invention, for control of patient heart rate and resulting alleviation or moderation of congestive heart failure. It should first be noted that in an open loop system, the impedance parameter derived as disclosed above from the patient's cardiac signal would be used directly to set the pattern and rate of the VS pulse sequence and thus control of the heart rate desired for therapeutic delivery, i.e., the target heart rate for the particular circumstances of the patient.

In a closed loop optimization mode of the invention, however, the impedance parameter is stored in an area 40 of a conventional memory in an implanted vagal stimulator, for retrieval on demand. Preferably, this parameter and the respective target heart rate it would produce are determined as a short term average on a daily or even an hourly or minute-by-minute basis, but may instead be acquired as a long term average over several days, if desired by the attending physician. The profile of the patient's actual heart rate, monitored from the cardiac signal itself as short (or long) term average over a like period, is stored in a second area 41 of the memory, likewise retrievable on demand. The actual heart rate profile and the impedance derived heart rate control parameter are compared to one another in a comparator and adjust/logic circuit 42, which produces a modified impedance parameter taking into account any material variations, utilized to adjust the vagal stimulation-controlled target heart rate at 43 accordingly. This controls not only the new target rate, but the slope of controlled heart rate with respect to the intensity of current physical activity by the patient as shown in graph 44. Comparator and logic circuit 42 is implemented to limit the target heart rate to a physiologically safe level (i.e., not to exceed a prescribed maximum rate).

Because the controlled heart rate varies inversely with the VS pulse frequency or rate, the circuit 42 output is processed to reduce the vagal stimulation rate accordingly when an increase in patient heart rate is called for by the particular level or intensity of the activity or exercise. Of course, because of the physical condition of a patient suffering from congestive heart failure disorder, it is unlikely that significant exertion will be tolerated or even attempted, but even the slight differences arising from, say, a change in physical position, arising from a supine or seated position, engaging in a slow walk, or slowly traversing a stairway, as well as more substantial activity, can be accommodated by the present invention.

In this respect, it is important to note that the invention serves the dual purpose of providing a controlled or target heart rate that not only reflects and accommodates any patient activity and its intensity (up to a prescribed upper limit), but also provides the desired therapeutic effect for alleviating the congestive heart failure. Equally important is the fact that the control is achieved based on a derived impedance parameter, a parameter that varies with patient ventilation, and therefore with states of exercise as well as rest of the patient, making it unnecessary to utilize a separate dedicated activity sensor, such as an accelerometer, to monitor the metabolic need of the patient of interest for purposes of delivering the therapy of the present invention. When the impedance factor indicates a lack of physical activity, the control of vagal stimulation is implemented to produce a preprogrammed heart rate for the therapy.

Short-term processing of the signal enables the effect of the heart rate adjustment to be evaluated against the ventilation and cardiac response within tens of seconds to achieve an individual optimization by compare and logic circuitry 42. The target rate (the controlled heart rate) that gives the lowest ventilation response is optimum for a given workload (recognizing, again, that anything that might be characterized as an intense workload or activity level is quite unlikely to be engaged in by a CHF patient). A person whose heart rate cannot increase adequately with intensity of physical exertion will breathe more heavily than one whose heart rate increases proportionately with exercise. Experiments by the applicants herein have shown that in the case of artificial cardiac pacing, if a pacing rate is kept constant at, say, 70 bpm, and no further increase in rate is allowed with exercise, the exercise capacity of the pacemaker patient is limited and will result in his/her breathing more heavily despite the limited exercise capacity. Clearly, the response of ventilation can be taken as an indirect indicator of the metabolic load and of the efficiency of the cardio-circulatory system, further demonstrating that the use of ventilation (and/or related impedance parameter as derived herein) as a closed loop parameter (or as a primary parameter) optimizes the controlled heart rate response of the present invention.

Figure 12:
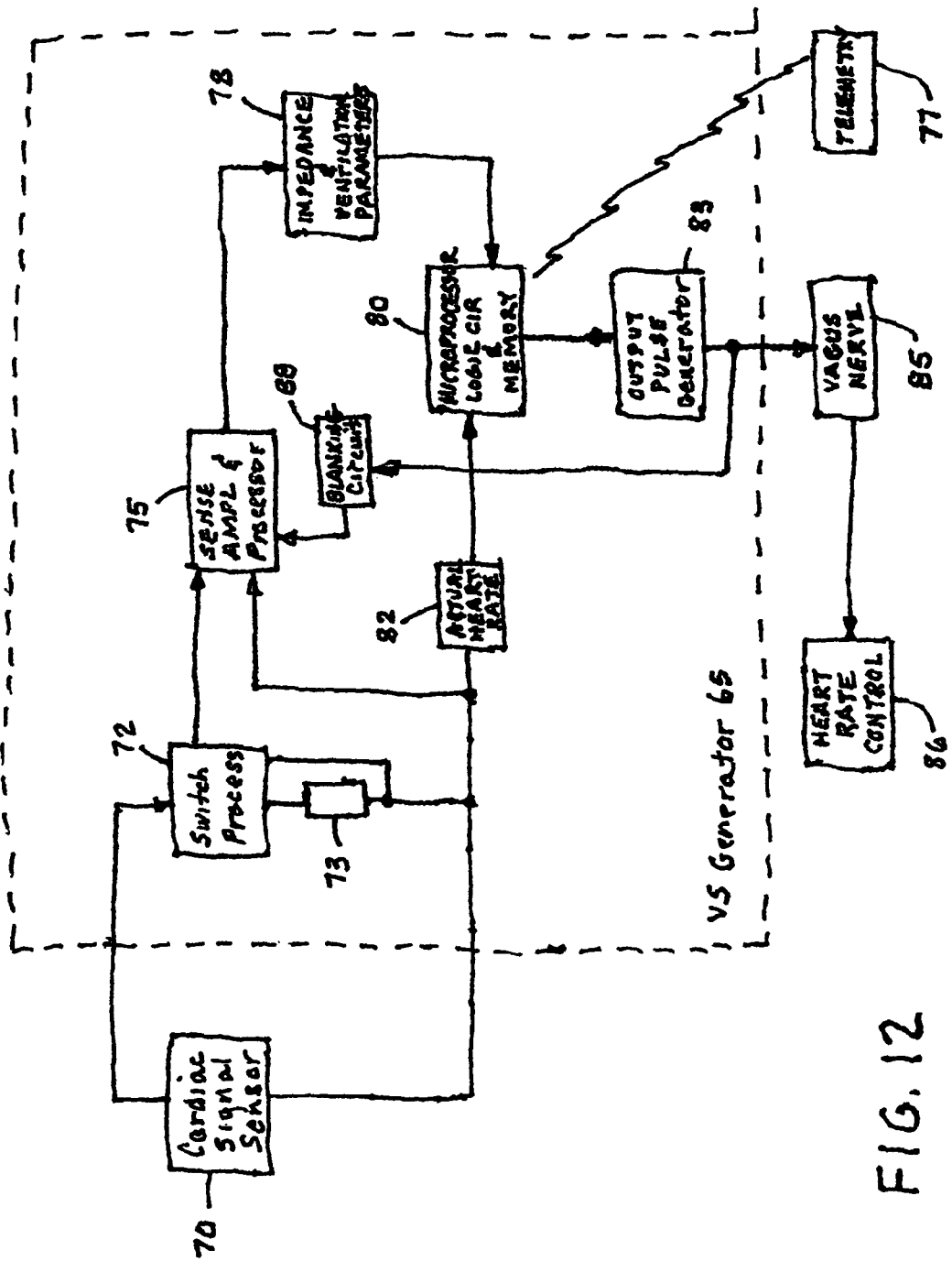
FIG. 12 is a block (or flow) diagram depicting the principles and signal processing of the present invention in a closed loop or open loop system for impedance factor-based vagal stimulation and concomitant control of heart rate of a CHF patient.
Figure 13:
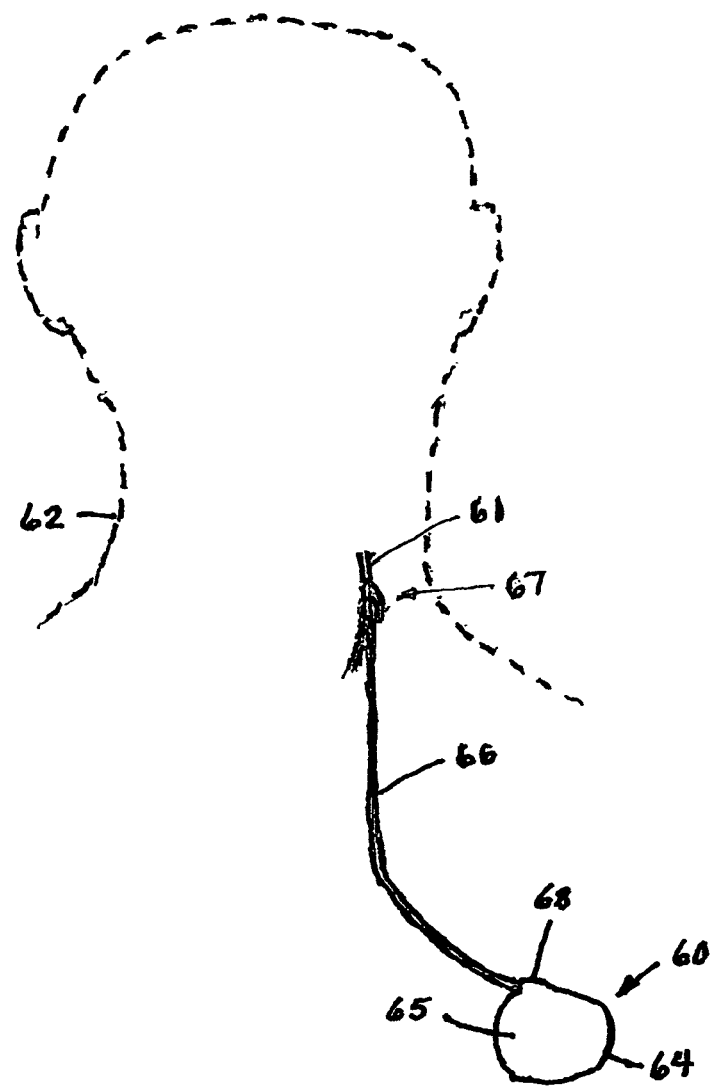
FIG. 13 is a simplified diagram of a vagal stimulation device with associated simplified representation of a cardiac signal sensing and vagal stimulation pulse delivery lead-electrode system implanted in a patient's body.

Before addressing the block diagram of the signal processing and flow of the presently preferred best mode illustrated in FIG. 12, it is useful to address the physiological accommodation of an implanted device and associated lead-electrode system shown in FIG. 13. A patient 62 (illustrated in phantom lines) has an implanted VS device 60, which includes a housing 64 ("can" or "case") for a vagal stimulator or VS generator 65. The composition and shape of the case may be as described in the '041 patent, and is suitably sized for implantation in a surgically-formed pocket just below the skin, typically in a pectoral region of the patient. An implanted insulated lead body 66 has an internal electrically conductive lead with its proximal end electrically coupled to generator 65 and with its distal end having electrode array 67 engaging (i.e., to be operatively coupled with) the right or left branch of vagus nerve 61, preferably above the cardiac branch, but not below that branch, at a cervical location such as shown in FIG. 13, for purposes of delivering stimulating pulses in a predetermined pattern and rate to the nerve. As observed in the '041 patent, the right vagus electrode placement appears to be more responsive to synchronized burst stimulation, but left vagus stimulation may be used instead.

According to the present invention, the cardiac signal may be sensed directly from electrical contacts that, at least in part, engage vagus nerve 61. The '041 patent discloses sensing the patient's heart rate at the vagus nerve as the significant aspect for purposes of ultimately controlling the vagal stimulation. In contrast, the present invention relies on signals generated by the electrical energy of the heart alone that are delivered as the sole input to signal detection circuitry for deriving the thoracic impedance and ventilation of the patient 62, and it is these factors or parameters that provide the basis for controlling the vagal stimulation.

Suitable arrangements for sensing include a separate electrically conductive lead within lead body 66 using two electrodes that engage the vagus nerve that may include the electrode used as well for stimulation, or through two electrodes that engage the vagus nerve and the metal case of VS generator as a third pole, or through the case alone and respective surface-mounted electrodes on the case (and insulated therefrom), electrodes on the header 68 or a combination of different electrode points on the case, on the header and/or on the electrode body.

The '041 patent notes that for some techniques, sensing and stimulation should not be performed from the same nerve electrode so as to avoid missing a sense event while vagal stimulation is being delivered, but instead would require a distinct separate sensing electrode. Such a separate electrode for sensing may be incorporated as an integral part of the VS generator 65, either on the case 64 or on the header 68; or a separate lead may be used with a sense tip positioned away from the stimulating electrode. Alternatively, a ring sense electrode located around the lead body some distance from the electrode(s) used for stimulation, may be utilized on its own lead. According to the '041 patent, if the stimulator is used exclusively in a synchronous burst mode for the VS, the same nerve electrode may be used in both sensing and stimulation.

Other suitable electrode arrangements are disclosed in the '272 patent. For example, the metal case 64 of VS generator 65 constitutes one sensing electrode in either of two implementations for sensing the cardiac activity of the heart. In one implementation, sensing may be performed between the metal case and a stimulating electrode coupled to the vagus nerve. The case is implanted with its backside positioned inwardly toward the patient's ribs, the backside being coated with a layer of biocompatible electrically insulating material to minimize muscle stimulation during vagal stimulation. In the other implementation, a pair of sensing electrodes may be exposed at the exterior of the case, one on the header and the other surface-mounted on and insulated from the case, preferably in orthogonal relationship to one another along the edge of the case for enhanced sensitivity to the electrical activity of the heart without regard to orientation of the implanted VS generator. The of pair external electrodes may be connected in parallel to operate as a single electrode in addition to the electrode provided by the metal case itself.

In a preferred method of the present invention, isolation between sensing and stimulation along the vagus nerve, as well as assurance that the cardiac signals sensed are purely from the electrical energy generated by the heart itself, unadulterated by other sources such as VS and its effect on the heart, are achieved by blanking the sense (input) amplifier of the generator 65 during and for the duration of stimulation. As suggested in the '272 patent, noise detection algorithms may be used to automatically inhibit vagal stimulation in the presence of noise artifacts at the sense electrodes.

The implanted VS generator 65 and an external console (not shown) may be implemented by conventional techniques for telemetry communication to accommodate external programming and monitoring, such as may be required after initial implantation of the stimulator and thereafter during office visits by the patient to the attending physician.

FIG. 12 is a combined block/flow diagram useful to illustrate signal processing and delivery in the system/method of the invention for vagal stimulation to treat a patient suffering from congestive heart failure. Cardiac (EKG) signal sensor 70 constitutes electrode means, which may be any of the various types or arrays described earlier herein, for obtaining the cardiac signal information to be processed. In the presently preferred best mode of practicing the invention, the cardiac signal sensing electrode means performs sensing of cardiac signal information emanating from the patient's vagus nerve. Such sensing electrode means preferably comprises at least one electrode means used for applying stimulating excitation to the vagus nerve. This stimulating electrode means may be used in combination with sensing electrode means of the aforesaid various types and arrays and positioning, for purposes of sensing the patient's cardiac signals from the vagus nerve as the heart undergoes its cardiac cycle.

Alternatively, cardiac signal information may be obtained in a conventional manner from sensing electrode means positioned in or in proximity to the heart itself. This alternative is less desirable because it requires additional surgical procedures, albeit only somewhat invasive, compared to those required in addressing the vagus nerve for both sensing and stimulating. As previously discussed herein, electrode means that specifically engage the vagus nerve are implanted at a site at or above the location at which a cardiac branch of the nerve branches (i.e., divides or departs) from the main branch or trunk of the vagus nerve. And this site is conveniently accessed in the patient's neck.

Preferably, at least bipolar cardiac signals are sensed. The sensed signals are delivered to a sense signal amplifier and processor 75 via an intervening switching process 72 by which a relatively high input impedance load 73 is alternately switched into and out of the signal processing circuitry in an ongoing rapid cycle of high input load—low input load. By this means, two different cardiac information signals are applied as the sole input to amplifier/processor 75, differing in the sense that one signal "sees" the high input impedance and the other signal "sees" a low input impedance, and thereby providing a dynamic impedance. The processor portion compares the two cardiac information signals and derives a patient intrathoracic impedance information parameter (which among other things, is indicative of the status of congestion) along with patient ventilation information (which among other things, along with the thoracic impedance information, is indicative of patient activity and its intensity), as described earlier herein. The derivation is obtained from the quotient of the load impedance/no load impedance-developed cardiac information signals, and the result, which may be characterized as impedance and ventilation factors or parameters, is indicated at 78.

It is useful to return to the discussion of the principles of the invention as presented earlier in this specification, to emphasize certain distinctions of this delivery and processing of the cardiac information signal relative to systems of the prior art. In a conventional EKG input system, the impedance of the system consists of the transitional impedance of the electrode-heart interface. That is to say, it is a local contact impedance, a static impedance, which is measured only through a high input impedance, such as one or two megohms. This conventional arrangement is useful to determine the integrity of the lead-electrode system, e.g., whether a lead is fractured, or the security of contact between the electrode and the heart or the nerve with which the electrode is in engagement. Also, inadequate insulation in the system may be observed as the existence of a low impedance.

In contrast, in the system of the invention a dynamic change in impedance is detected or measured by using a high input load as a baseline, and compared to a low input load in which the voltage drops considerably. These controlled rapid changes in input impedances are in parallel with the thoracic impedance as determined from the cardiac information signal, to enable detection of dynamic changes in the impedance. The availability of a dynamic impedance enables measurement of changes in congestion and ventilation, and doing so with a considerable reduction in drain on (and concomitant increase in longevity of) the battery of the neurostimulator as compared with prior techniques and methods, since in this aspect the present invention relies on electrical energy generated by the heart itself. Moreover, an overall simplification of the electronics may be achieved using this method.

The thoracic impedance/ventilation parameters, which contain as well, indications of the status of patient rest or activity (and intensity of the latter, if present), are then input to a microprocessor 80 incorporating logic circuitry and memory means including programmable memory. Here, several long term, short term, and derivatives of the information may be stored, and various pieces of information relevant to the condition of the particular patient in which the neurostimulator incorporating VS generator 65 is implanted may be programmed and re-programmed as necessary by an attending physician by means of conventional telemetry 77. The microprocessor and its associated logic are implemented to control an output pulse generator 83 of VS generator 65 to produce a desired excitation sequence for stimulating the patient's vagus nerve 85 in accordance with the thoracic impedance/ventilation factors.

Stimulation is applied through stimulating electrode means positioned relative to the vagus nerve as described earlier herein. At least in part, these electrode means serve, in addition to stimulation, as sensing electrode means for the EKG and thereby, to initiate the heart energy-derived dynamic thoracic impedance parameter. In the best mode presently contemplated, stimulation is provided by a series of electrical pulses in a pattern, sequence and frequency (or rate) controlled in accordance with the derived impedance/ventilation, as the output of VS generator 65. In turn, the excitation sequence so-determined for vagal stimulation is effective to cause (at 86) the patient's heart to beat at a prescribed target rate that takes into account not only delivery of the desired therapy to the anatomy of the heart, but also the demand on the heart arising from the state of rest or physical activity (and intensity thereof) of the patient. Changes from one state to another, or within the activity state as intensity changes, result in concomitant appropriate adjustment of the target heart rate according to the prescribed therapy to alleviate the congestive heart failure.

Movement from a current target rate to a new target rate occasioned by these changes in state can and should be controlled by the microprocessor and its logic to preclude abrupt changes in heart rate. Preferably, the change from a higher to a relatively lower target rate may be implemented to be more gradual than from a lower to a relatively higher rate. In any event, a maximum target rate is programmed in the device to be at a level that is safe and tolerable for the particular patient.

For an open loop system, the operation as described thus far in conjunction with FIG. 12 would be the basic extent of the vagal stimulation therapy. FIG. 12 also illustrates a closed loop method or implementation of vagus stimulation, which constitutes the preferred best mode or method of practicing the invention. In the closed loop configuration, the actual heart rate of the patient is detected from the sensed cardiac information signal at 82, and is applied to the microprocessor 80 and associated logic circuitry. There, a profile of the patient's actual heart rate is developed in long term, short term, and derivatives over time intervals corresponding to those for the thoracic impedance/ventilation parameters described above, and stored in microprocessor memory. The actual heart rate profile is compared to the impedance/ventilation parameter profile for the interval of interest, preferably that occurring instantaneously. The microprocessor and its associated logic use information derived from the comparison to control output pulse generator 83, and operation proceeds as described above except for the beneficial improved accuracy and stability resulting from the feedback obtained through the closed loop.

For either closed loop or open loop methods or implementations of the vagal stimulation, a blanking circuit 88 is incorporated in the device to provide blanking of the sense amplifier during and for the duration of the vagal stimulation. The blanking circuit is implemented to recognize the commencement of stimulation, and thereupon deactivate operation of the sense amplifier until stimulation ceases. This function is implemented to assure isolation between sensing and stimulation along the vagus nerve, and that cardiac information signals are sensed purely from the electrical energy generated by the heart itself, unadulterated by other sources such as the VS and its effect on the heart. Accordingly, the vagal stimulation preferably is not continuous, but instead interrupted periodically, albeit very briefly, to allow changes in the states of rest and activity of the patient to be monitored from the sensed cardiac information signals and thereby to enable adjustment of the target heart rate accordingly.

The implanted device operation may be monitored from time to time by conventional telemetry to allow physician review as well as to enable physician controlled changes in the device programming during office visits by the patient. Electronic means utilized in each implementation of the invention are state of the art, and may be provided in a single microchip or microchip array configuration to accommodate microminiature assembly, with the size of the implantable stimulator being dictated primarily by the required battery power. In addition to other desirable improvements described herein over the prior art, the present invention enables electrical energy generated by the patient's heart to be a primary source for deriving the thoracic impedance/ventilation parameters from the sensed cardiac information signal, with the result that battery drain is reduced and device lifetime is extended.

A presently contemplated best mode of practicing the invention has been disclosed, but variations and modifications may become apparent to those skilled in the art without departing from the spirit and scope of the invention.

What is claimed is:

1. A method of evaluating the cardio-circulatory and ventilatory condition of a human patient suffering from congestive heart failure disorder for delivery of therapy to alleviate the disorder, which comprises the steps of:
    sensing cardiac signals emanating from electrical energy generated by the patient's heart as the heart undergoes its cardiac cycle creating sensed electrical signals,
    applying the sensed electrical signals with a dynamic impedance as the sole input to signal detection circuitry to determine the patient's thoracic impedance and ventilation therefrom, and
    stimulating the patient's vagus nerve with stimulation pulses in a pattern and at a rate controlled by the determined impedance and ventilation.

2. The method of claim 1, including:
    applying said stimulation pulses to the vagus nerve at a site in the patient's neck.

3. The method of claim 1, including:
    applying said stimulation pulses at a site above a cardiac branch of the vagus nerve.

4. The method of claim 1, including:
    applying said stimulation pulses at a site where a cardiac branch departs from the main branch of the vagus nerve.

5. The method of claim 1, including:
    performing said sensing of cardiac signals utilizing at least in part electrode means used for said stimulating of the vagus nerve.

6. The method of claim 1, including:
    sensing a state of physical activity of the patient from said impedance and ventilation determination, and
    adjusting the pattern and rate of said stimulation pulses to control 4 the heart rate of said patient according to said sensed state of physical activity as a part of said therapy.

7. The method of claim 6, including:
    sensing the intensity of physical activity in said sensed state from said impedance and ventilation determination, and
    performing said adjusting of the pattern and rate of said stimulation pulses to control the heart rate of said patient according to said intensity of physical activity, not exceeding a predetermined level of heart rate prescribed as safe for said patient, as a part of said therapy.

8. The method of claim 1, including:
    providing said sensed electrical signals with dynamic impedance by subjecting said sensed electrical signals to alternately high and low input impedances prior to said application as said sole input to signal detection circuitry.

9. A method of delivering therapy to a patient suffering from chronic heart failure, said method comprising the steps of:
- applying vagal stimulation to the patient to provide a therapeutic heart rate for said patient,
- controlling the pattern, timing and frequency of said vagal stimulation according to thoracic impedance and ventilation of the patient, whereby to provide said therapeutic heart rate, and
- deriving said thoracic impedance and ventilation solely from EKG signals produced by electrical energy generated by the patient's heart with intervening dynamic impedance.

10. The method of claim 9, including:
- applying said vagal stimulation by delivering electrical pulses having said pattern, timing and frequency to the patient's vagus nerve at a cervical location at or above the site at which a cardiac branch divides from the main branch of the vagus nerve.

11. The method of claim 9, including:
- sensing said EKG signals via electrode means engaging the patient's vagus nerve from which to derive said thoracic impedance and ventilation.

12. The method of claim 11, including:
- performing said sensing of cardiac signals utilizing at least in part electrode means used for said stimulating of the vagus nerve.

13. The method of claim 12, including:
- utilizing neurostimulator means implanted in said patient for applying said vagal stimulation, said neurostimulator means including a case and a header on said case for operatively coupling said electrode means used for stimulating to said neurostimulator means, and
- performing said sensing of cardiac signals utilizing at least one additional electrode means among electrode means on said case, on said header, or on said vagus nerve, in combination with said electrode means used for said stimulating of the vagus nerve.

14. The method of claim 9, including:
- detecting a state of physical activity of the patient from said derived impedance and ventilation, and
- adjusting the pattern, timing and frequency of the vagal stimulation to provide a therapeutic heart rate reflecting said detected state of physical activity.

15. The method of claim 14, including:
- detecting the level of said physical activity from said derived impedance and ventilation, and
- performing an adjustment of said pattern, timing and frequency 4 of vagal stimulation to provide a therapeutic heart rate reflecting said detected level of physical activity, limited to a maximum heart rate deemed to be safely tolerated by said patient, as a part of said therapy.

16. The method of claim 9, including:
- providing said EKG signals with said intervening dynamic impedance by subjecting said EKG signals to an alternating high input impedance and low input impedance prior to deriving said thoracic impedance and ventilation.

17. A method of evaluating the status of congestion of a patient diagnosed with congestive heart failure and applying vagal stimulation therapy to alleviate the congestive heart failure, said method comprising the steps of:
- deriving the patient's thoracic impedance and ventilation solely by processing cardiac signals generated by electrical energy of the patient's heart as the heart is undergoing its cardiac cycle while subjecting said cardiac signals to a dynamic input impedance, to assess said status of congestion, and
- controlling the pattern and frequency of said applied vagal stimulation therapy according to the derived impedance and ventilation to adjust the patient's heart rate to a prescribed therapeutic rate.

18. The method of claim 17, including
- applying said vagal stimulation therapy to the patient's vagus nerve at a site at or above the branching of a cardiac branch from the main branch of the patient's vagus nerve.

19. The method of claim 17, including:
- detecting a change in state of the patient from one of rest to one of physical exercise and vice versa from said derived impedance and ventilation, and
- adjusting said vagal stimulation therapy for control of the patient's heart rate to a target rate that accommodates said change in state while delivering said therapy.

20. The method of claim 19, including:
- detecting intensity of said physical exercise from said derived impedance and ventilation, and
- further adjusting said vagal stimulation therapy to a new said target heart rate to reflect the detected intensity of physical exercise, while maintaining said new target rate within a prescribed safe maximum rate.

21. The method of claim 17, including:
- using a closed loop system to control said pattern and frequency of applied vagal stimulation therapy, and thereby to adjust the patient's target heart rate to at least partly reflect a feedback signal.

22. The method of claim 17, including:
- subjecting said cardiac signals to dynamic input impedance by placing alternately high and low input impedances in the path of said cardiac signals as a part of the processing to derive patient thoracic impedance and ventilation.

* * * * *